US009414813B2

(12) United States Patent  
Engel et al.

(10) Patent No.: US 9,414,813 B2
(45) Date of Patent: *Aug. 16, 2016

(54) DEVICE FOR ASSAYING ANALYTES IN BODILY FLUIDS

(71) Applicant: Express Diagnostics Int'l, Inc., Blue Earth, MN (US)

(72) Inventors: Matthias W. Engel, Reinbek (DE); Leslie Wilson, Sharon, MA (US); Paul Johnson, Blue Earth, MN (US)

(73) Assignee: EXPRESS DIAGNOSTICS INT'L, INC., Blue Earth, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,230

(22) Filed: Sep. 29, 2014

(65) Prior Publication Data

US 2015/0173724 A1    Jun. 25, 2015

Related U.S. Application Data

(63) Continuation of application No. 13/625,608, filed on Sep. 24, 2012, which is a continuation of application No. 13/211,208, filed on Aug. 16, 2011, now abandoned, which is a continuation of application No. PCT/EP2010/000948, filed on Feb. 16, 2010.

(30) Foreign Application Priority Data

Feb. 16, 2009    (DE) .......................... 10 2009 010 563

(51) Int. Cl.
*G01N 33/558*    (2006.01)
*A61B 10/00*    (2006.01)

(52) U.S. Cl.
CPC ......... *A61B 10/0051* (2013.01); *A61B 10/0045* (2013.01); *G01N 33/558* (2013.01);

(Continued)

(58) Field of Classification Search
None
See application file for complete search history.

(56) References Cited

U.S. PATENT DOCUMENTS 3,641,235 A    2/1972    Weiss
3,959,078 A    5/1976    Guire (Continued)

FOREIGN PATENT DOCUMENTS

DE    2729283    2/1979
DE    3427114    10/1988

(Continued)

OTHER PUBLICATIONS

Broach et al., "High Throughput Screening for Drug Discovery," Nature (1996) 384:14-16.

(Continued)

*Primary Examiner* — Chris L Chin
(74) *Attorney, Agent, or Firm* — Christensen Fonder P.A.

(57) ABSTRACT

A device for determining the presence and/or quantity of one or more analytes in a sample of human body fluid has a container for receiving a sample of body fluid, with an interior that is delimited by a base and by a circumferential surface. It further comprises at least one test strip and a holding element for receiving and holding the one or more test strips. The holding element is designed such that it has a shape corresponding and adapted to the peripheral circumferential surface of the container. The device further comprises an elongate sampling element having an absorbent sampler that takes up the sample of body fluid and by means of which the sample of body fluid is transferred into the container. The sampling element can include an indicator strip for determining whether the amount of liquid sample sufficient for carrying out an assay.

13 Claims, 13 Drawing Sheets

(52) U.S. Cl.
CPC ........... *A61B10/007* (2013.01); *A61B 10/0096* (2013.01); *A61B 2010/0006* (2013.01); *A61B 2010/0009* (2013.01)

(56) References Cited

U.S. PATENT DOCUMENTS

| | | |
|---|---|---|
| 3,966,897 A | 6/1976 | Renn et al. |
| 4,094,647 A | 6/1978 | Deutsch et al. |
| 4,168,146 A | 9/1979 | Grubb et al. |
| 4,299,916 A | 11/1981 | Litman et al. |
| 4,332,788 A | 6/1982 | Mochida et al. |
| 4,347,312 A | 8/1982 | Brown et al. |
| 4,366,241 A | 12/1982 | Tom et al. |
| 4,373,932 A | 2/1983 | Gribnau et al. |
| 4,391,904 A | 7/1983 | Litman et al. |
| 4,425,438 A | 1/1984 | Bauman et al. |
| 4,517,288 A | 5/1985 | Giegel et al. |
| 4,678,559 A | 7/1987 | Szabados |
| 4,695,554 A | 9/1987 | O'Connell et al. |
| 4,703,017 A | 10/1987 | Campbell et al. |
| 4,743,560 A | 5/1988 | Campbell et al. |
| 4,857,453 A | 8/1989 | Ullman et al. |
| 4,861,711 A | 8/1989 | Friesen et al. |
| 4,956,302 A | 9/1990 | Gordon et al. |
| 4,960,691 A | 10/1990 | Gordon et al. |
| 5,073,484 A | 12/1991 | Swanson et al. |
| 5,075,078 A | 12/1991 | Osikowicz et al. |
| 5,079,142 A | 1/1992 | Coleman et al. |
| 5,120,643 A | 6/1992 | Ching et al. |
| 5,141,875 A | 8/1992 | Kelton et al. |
| 5,186,897 A | 2/1993 | Eason et al. |
| 5,236,826 A | 8/1993 | Marshall |
| 5,252,459 A | 10/1993 | Tarcha et al. |
| 5,252,496 A | 10/1993 | Kang et al. |
| 5,260,031 A | 11/1993 | Seymour |
| 5,275,785 A | 1/1994 | May |
| 5,422,726 A | 6/1995 | Tyler |
| 5,501,949 A | 3/1996 | Marshall |
| 5,504,013 A | 4/1996 | Senior |
| 5,514,602 A | 5/1996 | Brooks, Jr. et al. |
| 5,559,041 A | 9/1996 | Kang et al. |
| 5,571,726 A | 11/1996 | Brooks, Jr. et al. |
| 5,578,577 A | 11/1996 | Ching et al. |
| 5,591,645 A | 1/1997 | Rosenstein |
| 5,596,414 A | 1/1997 | Tyler |
| 5,602,040 A | 2/1997 | May et al. |
| 5,622,871 A | 4/1997 | May et al. |
| 5,654,162 A | 8/1997 | Guire et al. |
| 5,656,448 A | 8/1997 | Kang |
| 5,656,503 A | 8/1997 | May et al. |
| 5,710,005 A | 1/1998 | Rittenburg |
| 5,712,170 A | 1/1998 | Kouvonen et al. |
| 5,714,389 A | 2/1998 | Charlton et al. |
| 5,728,587 A | 3/1998 | Kang et al. |
| 5,747,273 A | 5/1998 | Khosravi et al. |
| 5,753,517 A | 5/1998 | Brooks et al. |
| 5,798,273 A | 8/1998 | Shuler et al. |
| 5,965,458 A | 10/1999 | Kouvonen et al. |
| 5,976,895 A | 11/1999 | Cipkowski |
| 5,989,921 A | 11/1999 | Charlton et al. |
| 6,017,767 A | 1/2000 | Chandler |
| 6,020,147 A | 2/2000 | Guire et al. |
| 6,027,943 A | 2/2000 | Kang et al. |
| 6,103,536 A | 8/2000 | Geisberg |
| 6,121,008 A | 9/2000 | Fitzpatrick et al. |
| 6,140,048 A | 10/2000 | Muller et al. |
| 6,140,134 A | 10/2000 | Rittenburg |
| 6,156,271 A | 12/2000 | May |
| 6,187,269 B1 | 2/2001 | Lancesseur et al. |
| 6,187,598 B1 | 2/2001 | May et al. |
| 6,194,222 B1 | 2/2001 | Buechler et al. |
| 6,228,660 B1 | 5/2001 | May et al. |
| 6,267,722 B1 | 7/2001 | Anderson et al. |
| 6,287,875 B1 | 9/2001 | Geisberg |
| RE37,437 E | 11/2001 | Friesen et al. |
| 6,319,676 B1 | 11/2001 | Nazareth et al. |
| 6,352,862 B1 | 3/2002 | Davis et al. |
| 6,368,875 B1 | 4/2002 | Geisberg |
| 6,379,620 B1 | 4/2002 | Tydings et al. |
| 6,394,952 B1 | 5/2002 | Anderson et al. |
| 6,399,398 B1 | 6/2002 | Cunningham et al. |
| 6,416,715 B1 | 7/2002 | Gambert et al. |
| 6,485,982 B1 | 11/2002 | Charlton |
| 6,497,843 B2 | 12/2002 | Tydings |
| 6,506,612 B2 | 1/2003 | Kang et al. |
| 6,534,320 B2 | 3/2003 | Ching et al. |
| 6,541,277 B1 | 4/2003 | Kang et al. |
| 6,544,797 B1 | 4/2003 | Buechler et al. |
| 6,548,019 B1 | 4/2003 | Lee et al. |
| 6,616,893 B1 | 9/2003 | Pham |
| 6,649,418 B1 | 11/2003 | Geisberg |
| RE38,430 E | 2/2004 | Rosenstein |
| 6,707,554 B1 | 3/2004 | Miltner et al. |
| 6,737,277 B1 | 5/2004 | Kang et al. |
| 6,759,202 B2 | 7/2004 | Grossman et al. |
| 6,764,827 B1 | 7/2004 | Aoki et al. |
| 6,767,709 B1 | 7/2004 | Suzuki et al. |
| 6,770,487 B2 | 8/2004 | Crosby |
| 6,777,198 B2 | 8/2004 | Mendel-Hartvig et al. |
| 6,805,837 B2 | 10/2004 | Tydings |
| 6,805,838 B2 | 10/2004 | Tydings |
| 6,812,038 B1 | 11/2004 | Mendel-Hartvig et al. |
| 6,818,455 B2 | 11/2004 | May et al. |
| 6,830,731 B1 | 12/2004 | Buechler et al. |
| 6,849,450 B2 | 2/2005 | Langley et al. |
| 6,861,214 B1 | 3/2005 | Rampal et al. |
| 6,867,051 B1 | 3/2005 | Anderson et al. |
| 6,916,666 B1 | 7/2005 | Mendel-Hartvig et al. |
| 6,936,476 B1 | 8/2005 | Anderson et al. |
| 7,049,150 B2 | 5/2006 | Bachand |
| 7,081,348 B2 | 7/2006 | Suzuki et al. |
| 7,109,042 B2 | 9/2006 | May et al. |
| 7,175,992 B2 | 2/2007 | Fong |
| 7,178,416 B2 | 2/2007 | Whelan et al. |
| 7,205,553 B2 | 4/2007 | Dorsel et al. |
| RE39,664 E | 5/2007 | Gordon et al. |
| 7,238,537 B2 | 7/2007 | Davis et al. |
| 7,238,538 B2 | 7/2007 | Freitag et al. |
| 7,239,394 B2 | 7/2007 | Sharrock et al. |
| 7,247,500 B2 | 7/2007 | Wei et al. |
| 7,256,053 B2 | 8/2007 | Hu |
| 7,270,970 B2 | 9/2007 | Anderson et al. |
| 7,312,027 B2 | 12/2007 | Bachand |
| 7,315,378 B2 | 1/2008 | Phelan et al. |
| 7,317,532 B2 | 1/2008 | Sharrock et al. |
| 7,323,139 B2 | 1/2008 | LaBorde et al. |
| 7,371,582 B2 | 5/2008 | Nahm et al. |
| 7,384,796 B2 | 6/2008 | Davis et al. |
| 7,407,813 B2 | 8/2008 | Davis et al. |
| 7,416,700 B2 | 8/2008 | Buechler et al. |
| 7,476,549 B2 | 1/2009 | Nahm et al. |
| 7,510,881 B2 | 3/2009 | Ramael et al. |
| 7,521,259 B2 | 4/2009 | Petruno et al. |
| 7,521,260 B2 | 4/2009 | Petruno et al. |
| 7,553,630 B2 | 6/2009 | Langley et al. |
| 7,588,908 B2 | 9/2009 | Buechler et al. |
| 7,616,315 B2 | 11/2009 | Sharrock et al. |
| 7,633,620 B2 | 12/2009 | Nahm et al. |
| 7,662,643 B2 | 2/2010 | Wei et al. |
| 7,679,745 B2 | 3/2010 | Claps et al. |
| 7,691,595 B2 | 4/2010 | Fong |
| 7,713,703 B1 | 5/2010 | Buechler et al. |
| 7,763,454 B2 | 7/2010 | Nazareth et al. |
| 7,784,678 B2 | 8/2010 | Kuo |
| 7,785,899 B2 | 8/2010 | Saul et al. |
| 7,796,266 B2 | 9/2010 | Cohen et al. |
| 7,815,853 B2 | 10/2010 | Nahm et al. |
| 7,815,854 B2 | 10/2010 | Cohen et al. |
| 7,927,562 B2 | 4/2011 | Wan et al. |
| 8,163,253 B1 | 4/2012 | Hartselle |
| 2002/0187076 A1 | 12/2002 | DiCesare et al. |
| 2003/0064526 A1 | 4/2003 | Niedbala et al. |
| 2003/0119202 A1 | 6/2003 | Kaylor et al. |
| 2003/0190259 A1 | 10/2003 | Alley |

(56) References Cited

U.S. PATENT DOCUMENTS

| | | |
|---|---|---|
| 2005/0119589 A1 | 6/2005 | Tung et al. |
| 2005/0221504 A1 | 10/2005 | Petruno et al. |
| 2005/0221505 A1 | 10/2005 | Petruno et al. |
| 2005/0244953 A1 | 11/2005 | Cohen |
| 2006/0018800 A1 | 1/2006 | Slowey et al. |
| 2006/0019265 A1 | 1/2006 | Song et al. |
| 2006/0127274 A1 | 6/2006 | Vallejo et al. |
| 2006/0172438 A1 | 8/2006 | Milunic et al. |
| 2006/0240541 A1 | 10/2006 | Petruno et al. |
| 2007/0143035 A1 | 6/2007 | Petruno |
| 2007/0185679 A1 | 8/2007 | Petruno et al. |
| 2008/0028261 A1 | 1/2008 | Petruno et al. |
| 2008/0194041 A1 | 8/2008 | Guirguis |
| 2009/0117006 A1 | 5/2009 | Fernandez |
| 2009/0157023 A1 | 6/2009 | Song et al. |
| 2009/0180925 A1 | 7/2009 | Petruno et al. |
| 2009/0180926 A1 | 7/2009 | Petruno et al. |
| 2009/0180927 A1 | 7/2009 | Petruno et al. |
| 2009/0180928 A1 | 7/2009 | Petruno et al. |
| 2009/0180929 A1 | 7/2009 | Petruno et al. |
| 2009/0214383 A1 | 8/2009 | Petruno et al. |
| 2009/0269858 A1 | 10/2009 | Punyadeera et al. |
| 2009/0311724 A1 | 12/2009 | Levison et al. |
| 2009/0325201 A1 | 12/2009 | Franzmann et al. |
| 2010/0015611 A1 | 1/2010 | Webster et al. |
| 2010/0081148 A1 | 4/2010 | Singbartl et al. |
| 2010/0094564 A1 | 4/2010 | Kuo et al. |
| 2010/0143941 A1 | 6/2010 | Wu et al. |
| 2010/0165338 A1 | 7/2010 | Claps |
| 2010/0173423 A1 | 7/2010 | Zuaretz et al. |
| 2010/0239460 A1 | 9/2010 | Nazareth et al. |
| 2010/0240149 A1 | 9/2010 | Nazareth et al. |
| 2010/0255510 A1 | 10/2010 | Wang et al. |
| 2010/0279301 A1 | 11/2010 | Chinnaiyan et al. |
| 2010/0311181 A1 | 12/2010 | Abraham et al. |
| 2011/0011959 A1 | 1/2011 | Greenwood et al. |
| 2011/0065136 A1 | 3/2011 | Labrie et al. |
| 2011/0065137 A1 | 3/2011 | Labrie et al. |
| 2011/0065593 A1 | 3/2011 | Labrie et al. |
| 2011/0065598 A1 | 3/2011 | Labrie et al. |
| 2011/0065599 A1 | 3/2011 | Labrie et al. |
| 2011/0065608 A1 | 3/2011 | Labrie et al. |
| 2011/0124519 A1 | 5/2011 | Falkenberg et al. |

FOREIGN PATENT DOCUMENTS

| | | |
|---|---|---|
| DE | 69013842 | 3/1995 |
| DE | 19748331 | 1/1999 |
| DE | 200221659 | 9/2001 |
| DE | 20316987 | 2/2004 |
| DE | 69909232 | 4/2004 |
| DE | 212004000061 | 10/2006 |
| DE | 60222154 | 6/2008 |
| EP | 0149168 | 7/1985 |
| EP | 0186799 | 7/1986 |
| EP | 0250137 | 12/1987 |
| EP | 0299359 | 1/1989 |
| EP | 0323605 | 7/1989 |
| EP | 0183442 | 3/1990 |
| EP | 0520408 | 12/1992 |
| EP | 0225054 | 1/1993 |
| EP | 1847321 | 10/2007 |
| GB | 1526708 | 9/1978 |
| WO | WO 89/06799 | 7/1989 |
| WO | WO 99/40438 | 8/1999 |
| WO | WO 03/031068 | 4/2003 |
| WO | WO 2006/033826 | 3/2006 |
| WO | WO 2008/084331 | 7/2008 |
| WO | WO 2008/139324 A2 | 11/2008 |

OTHER PUBLICATIONS

Burbaum et al., "New Technologies for High-Throughput Screening," Curr. Opin. Chem. Biol. (1997) 1:72-78.

Dictionary definition of "adjacent", Merriam-Webster Online Dictionary (www.mw.com/dictionary/adjacent), dated Nov. 22, 2005.

"Immunoglobulin D", Wikipedia, the free encyclopedia (en.wikipedia.org/wiki/IgD), dated Feb. 6, 2011.

"Immunoglobulin G", Wikipedia, the free encyclopedia (en.wikipedia.org/wiki/IgG), dated Feb. 6, 2011.

Fernandes, "Letter from the Society President," J. Biomol. Screening (1997) 2:1.

Harlow et al., "Using Antibodies: A Laboratory Manual," p. 8 (Cold Spring Harbor Laboratory Press, Cold Springs Harbor, New York, 1999).

Illustration from Weiss Patent (U.S. Pat. No. 3,6431,235).

Janzen et al., "High throughput Screening as a Discovery Tool in the Pharmaceutical Industry," Lab Robotics Automation (1996) (8):261-265.

Leuvering et al., "Sole Particle lmmunossay (SPIA)," J. Immunoassay (1980) 1 (1 ):77-91.

Lexsee 365 F.2D 834, In re Griswold and Pearce, 365 F.2d 834 (1966).

Lexsee 417 F.3E 1369, Pharmacia Corp. v. PAR Pharmaceutical, Inc., 417 F.3d 1369 (2005).

Request for Reexamination and Exhibits 1-5 for U.S. Pat. No. 6,805,837, dated Nov. 23, 2005.

Request for Reexamination and Exhibits 1-5 for U.S. Pat. No. 6,805,838, dated Nov. 23, 2005.

Request for Reexamination and Exhibits 1-3 for U.S. Pat. No. 5,073,484 dated Sep. 26, 2003.

Request for Reexamination and Exhibits 1-8 for U.S. Pat. No. 6,485,982 dated Sep. 15, 2005.

Requestor's Reply to Patent Owner's Statement and Exhibits 1-2 for U.S. Pat. No. 6,805,837, dated Feb. 22, 2006.

Requestor's Reply to Patent Owner's Statement and Exhibits 1-2 for U.S. Pat. No. 6,805,838, dated Feb. 22, 2006.

Statement by Patent Owner and Exhibits A-D for U.S. Pat. No. 6,805,837, dated Dec. 23, 2005.

Statement by Patent Owner and Exhibits A-D for U.S. Pat. No. 6,805,838, dated Dec. 23, 2005.

Takeda et al., "Experience in Use of Urotrace for Urine of Patients," Rinsho Kensa (Clinical Test) (1974) (original article in Japanese followed by English translation).

ThermoFisher Scientific information sheet entitled "Color-Rich™ Fluoro-Max™ Dyed Microparticles," dated Mar. 2008.

Thermo Scientific Instructions sheet entitled Dylight™ Microscale Antibody Labeling Kits,: copyrighted 2010.

Van Hell et al., in Alternative immunoassays (W.P. Collins ed., John Wiley & Sons, 1985), Ch. 4 "Particle Immunoassays," pp. 39-59.

Wood et al., "Base Composition-Independent Hybridization in Tetramethylammonium Chloride: A Method for Oligonucleotide Screening of Highly Complex Gene Libraries," Proc. Natl. Acad. Sci. USA (1985) 82:1585-1588.

International Preliminary Report on Patentability for International Application No. PCT/EP2010/000948 mailed Aug. 25, 2011, 7 pages (English translation).

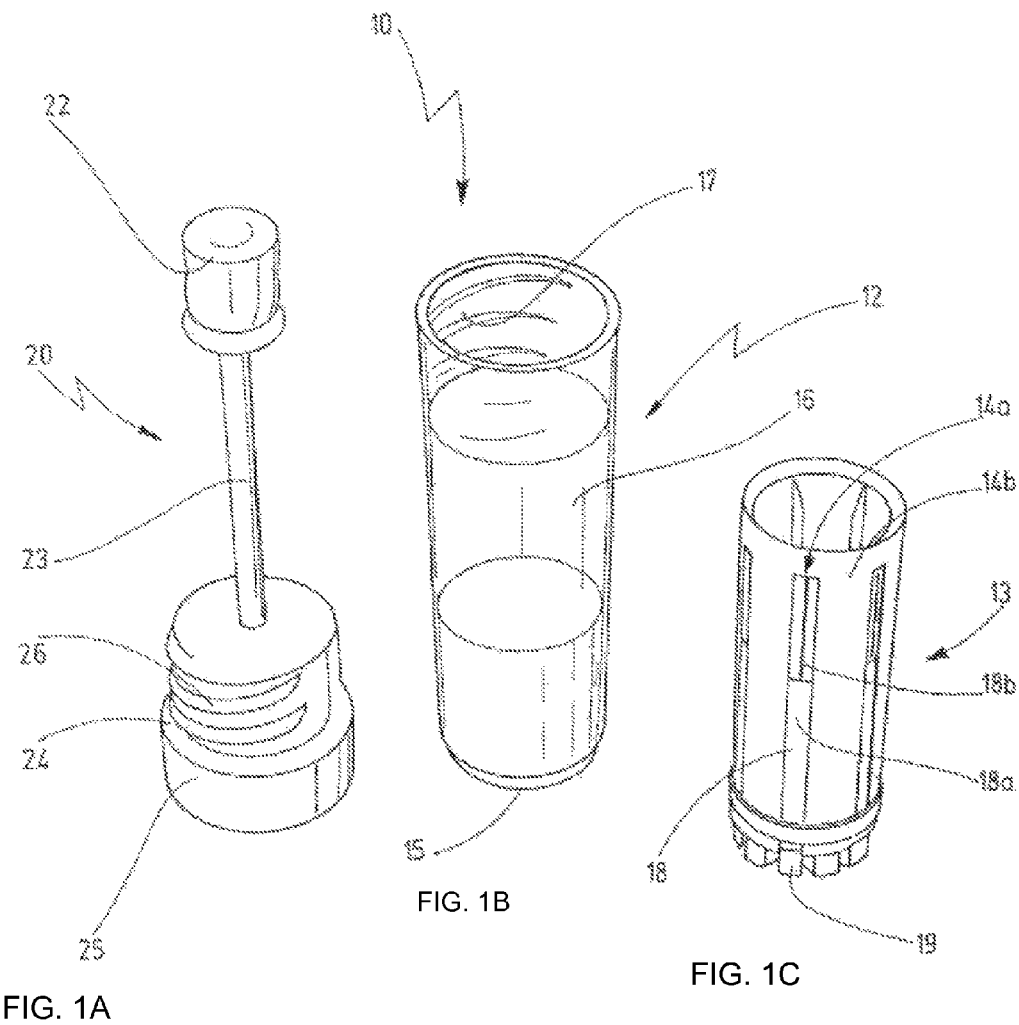

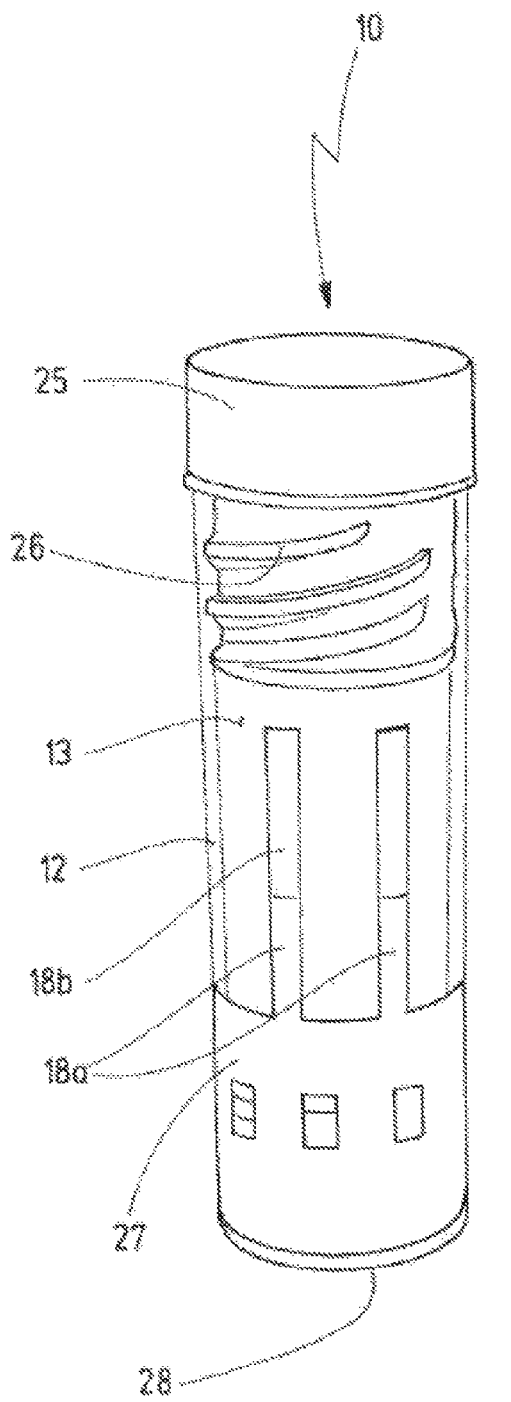
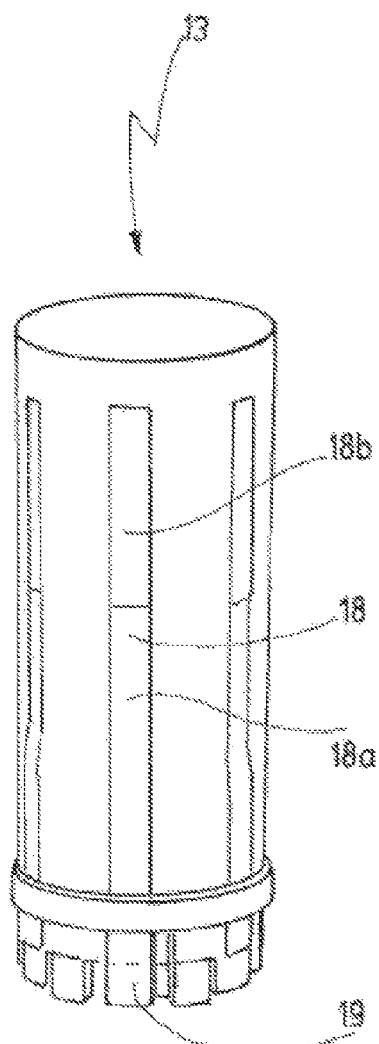
FIG. 2A
FIG. 2B

DEVICE FOR ASSAYING ANALYTES IN BODILY FLUIDS

CROSS-REFERENCES TO RELATED APPLICATIONS

This application is a continuation of U.S. patent application Ser. No. 13/625,608, filed Sep. 24, 2012, which is a continuation of U.S. patent application Ser. No. 13/211,208, filed Aug. 16, 2011, which is a continuation of co-pending International Patent Application PCT/EP 2010/000948 filed on Feb. 16, 2010, and designating the US, which international Patent Application has been published in German language as WO 2010/091897, and claims priority from German Patent Application DE 10 2009 010 563.8 filed on Feb. 16, 2009. The entire contents of these priority applications are incorporated herein by this reference.

BACKGROUND OF THE INVENTION

The present invention relates to a device for determining the presence and/or quantity of one or more analytes in a sample of human body fluid, comprising a container for receiving a sample of body fluid, and further comprising at least one test strip with an absorbent section and with reagents for determining the presence and/or quantity of one or more analytes in the sample.

More specifically, the present invention concerns a device for collecting and testing a liquid sample, as is used in particular in tests for a drug or for multiple drugs. For this purpose, the presence and/or quantity of one or more analytes, in particular drugs of abuse, is determined from a sample of a body fluid, for example saliva or urine. The result can be determined visually by means of test strips.

Various analytical devices with which analytes in a sample can be detected are known from, for example, EP 0 225 054, EP 0 183 442, EP 0 186 799, EP 0 299 359 and WO 89/06799. All of these devices use test strips impregnated with reagents in specific binding assays in which a liquid sample is applied to an end of the test strip and migrates across or through the test strip. The test strip can in these cases be provided in a cover. If the analyte that is to be detected is present in a sample, it can be detected by a binding reagent immobilized in a detection zone, for example by a sandwich assay or a competitive assay.

Moreover, test cards are known that comprise test strips with which amphetamines and drugs such as ecstasy, cocaine, crack or opiates and cannabis are intended to be detected in parallel.

Suitable detection methods are, for example, immunoassays, which are highly sensitive detection methods based on the specificity of immunological reactions. The substances are detected using an easily detectable and measurable indicator substance, for example radioactive isotopes, enzymes, dyes, for example gold sols, and fluorescence dyes.

The tests presently on the market are solid-phase tests. A marked antigen or a marked antibody, which is specific for the substance to be detected, is located in a first zone which first comes into contact with the liquid sample. If the sample contains an analyte that is recognized by the specific antibodies or antigens, these bind to the analyte and migrate with the latter through the solid carrier as far as a second zone, where a further reagent is bound which also specifically recognizes either the analyte or the antibody/antigen. The binding of the analyte-antibody/analyte-antigen reaction product in the second zone means that the analyte can be detected, for example, by an accumulation of the markers, or by a chemical reaction triggered by the binding.

Solid-phase immunoassays in the competitive or sandwich technique are known to persons skilled in the art and for this reason do not have to be explained in detail here.

Moreover, DE 200 21 659 U1 discloses a device in which samples of body fluid, in particular urine, are tested for a plurality of drugs of abuse simultaneously. Test strips are arranged on a test card, each strip being sensitive to a specific drug of abuse and having a visible limit value in order to indicate the presence or absence of a specific drug. The container used has, at its upper end, a closure lid which has a slot of such a size that a test card with test strips can be fitted therein. The test card can be inserted through the slot in such a way that one end is immersed in the urine sample to a predetermined depth, the visible result from each test strip being able to be seen by virtue of the transparency of the wall of the container without removing the test card from the container. When samples test "positive", it is necessary for the slotted lid to be replaced by a second, unslotted lid and to remove the test card from the container, in order then to be able to send the closed container to a certified laboratory.

Another disadvantage of the tests known from the prior art is that, for an initial detection of the drugs, sufficient quantities, i.e., relatively large quantities, of body fluids are needed in order to allow the tests to be carried out. Particularly for detecting drugs in saliva, the consistency and availability of the latter mean that quite large quantities are needed, which makes rapid drug detection, for example of the kind that is intended to be performed in direct on-site tests, difficult to achieve when using saliva. For this reason, most of the presently available tests are based on the use of urine samples.

SUMMARY OF THE INVENTION

Against this background, it is an object of the invention to permit an improved and more simply designed device for the analysis of liquid samples, which does not require any additional aids for preparing the sample.

According to one aspect of the invention, there is provided a device for determining the presence and/or quantity of one or more analytes in a sample of human body fluid, comprising a container for receiving a sample of body fluid, with an interior that is delimited by a base and by a circumferential surface, further comprising at least one test strip with an absorbent section and with reagents for determining the presence and/or quantity of one or more analytes in the sample of body fluid, and comprising a holding element for receiving and holding the one or more test strips, said holding element having a shape corresponding and adapted to the peripheral circumferential surface of the container; the device according to the invention further comprises an elongate sampling element which, at one of its ends, has an absorbent sampler that takes up the sample of body fluid, which sampling element can be inserted into the container, via its end comprising the sampler, in order to transfer the sample of body fluid into the container, and in that the base of the container has a central elevation or protrusion via which the sample of body fluid can be conveyed from the sampler, by compression thereof on the elevation, to the at least one test strip.

By means of the elongate sampling element and the absorbent sampler provided thereon, it is possible, by interaction with the elevation provided on the base of the container, for the sample of body fluid, for example saliva, which has been taken up into the absorbent sampler, to be squeezed out in the container and to be conveyed to the absorbent sections of the test strips present in the container; almost the whole sample that has been taken up is utilized in this process, with the result that only relatively small quantities of the sample are needed.

The elongate sampling element, which comprises a sampler at one of its ends, can be used to collect a sample of saliva, for example, from a person's mouth or throat, i.e., the nature of the absorbent sampler is such that the saliva is sucked up by the sampler. The material from which the sampler is made can be any absorbent material, preferably a material with cotton-like or sponge-like properties, which, when squeezed out or pressed out, allows the sample contained therein to easily emerge from the material and additionally does not alter the composition of the saliva. It is within the competence of a person skilled in the art to provide a material suitable for these purposes. The sampling element comprising the sampler, fully soaked with saliva for example, is then placed into the container, where it is pressed onto the elevation provided centrally on the base of the container, and the liquid sample, for example saliva, contained in the sampler is thus squeezed out. The sample then flows across the elevation to the side edge at the base of the container, where the absorbent section of the at least one test strip is located and takes up the sample by capillary forces. The sample then migrates across or up the test strip, as a result of which any analytes present in the sample can be detected in the manner described above.

With the device according to the invention, an easy-to-use test appliance is thus made available which is also suitable for testing samples of saliva and with which the analytes that are to be detected in a sample can be detected rapidly. The centrally arranged elevation also ensures that the sample contained in the sampler is squeezed out uniformly and is guided uniformly to the peripheral inner edge of the container. The absorbent sections of the one or more test strips present there are thus supplied uniformly with the sample.

In the present context, an "elongate" sampling element signifies any stick- or rod-shaped element that is suitable for being gripped at its one end by the person being tested or by a third party, such that the other end can be inserted into the mouth/throat in order to collect a sample of saliva, for example. The sampling element according to the invention therefore has an end at which the sampler is provided and a gripping end, as well as an elongate, stick- or rod-shaped section lying in between. It will be appreciated, however, that the sample is not limited to a sample of saliva, since the sampling element can also be dipped into another receptacle containing the liquid sample, as a result of which the sampler can likewise be fully impregnated with the sample. The sample that has been taken up in this way is then guided into the container, as has been described above, and the test for determining the presence or quantity of an analyte is started by squeezing the sample out from the sampler and bringing the test strips into contact with the sample.

In a preferred refinement, the sampling element and/or the sampler are provided with at least one means that indicates that, and whether sufficient, liquid sample, in particular saliva, has been taken up.

In another preferred refinement, the at least one means is an indicator strip of an absorbent material that is present in the sampling element and has at least one zone which lies away from the sampler and in which it is indicated when sufficient liquid sample, in particular saliva, is present by the colour of the material changing. The absorbent material is in this case preferably a material comprising cellulose and makes it possible for the liquid sample to be able to migrate through or across the indicator strip and arrive in the zone in which the change in colour is observed. In this case, the change in colour of the material may comprise a darkening of its colour that is brought about by the liquid sample taken up by and migrating across the material.

In another preferred refinement, the change in colour may take place by a reaction of the material with the liquid sample in the manner of a pH indicator paper, according to which the material changes its colour, or takes on a colour if the material was previously colourless, at least in the zone. It will be appreciated that the indicator strip either undergoes a change in colour as a whole when the liquid sample migrates across or through the indicator strip, or else only in the zone on the basis of which the presence of a sufficient amount of liquid sample is indicated. In the case of the latter embodiment, the zone is correspondingly impregnated, or has a different composition than the rest of the material of the indicator strip. Furthermore, it may be provided that only the zone can be observed via a window, while the rest of the indicator strip is covered with an opaque material.

In another preferred refinement, at a certain distance from the sampler on the rod-shaped section of the sampling element, the sampling element may be provided with a marking, for example in the form of a line or a notch, which is intended to serve as an indication as to how far the front of the liquid sample must travel across the indicator strip present in the sampling element to ensure the presence of a sufficient amount of liquid sample in the sampler. It will be appreciated that in the case of this embodiment the indicator strip as a whole can be seen.

The indicator strip by means of which it is indicated when sufficient liquid sample is present may, for example, be arranged in a—cross-sectionally—U-shaped recess in the rod-shaped section of the sampling element, and protrude with one of its ends into the sampler, which comprises a sponge-like material, or be received therein. This allows the liquid sample that is received by the sampler to reach the indicator strip and migrate across the indicator strip by capillary forces.

In a preferred refinement of the device according to the invention, it is also preferable if the elevation is a hemispherical elevation with its highest point located centrally in the base of the container.

This measure has the advantage that the sample contained in the sampler can be easily squeezed out on the hemispherical elevation, after which the sample flows down the elevation, on account of the hemispherical shape of the elevation, and towards the edge of the base or to the site where the base merges into the circumferential surface. Here, the sample is taken up by the absorbent section of the at least one test strip, and the detection of the analyte on the test strip proceeds.

In the device according to the invention, the space between the outer peripheral edge of the hemispherical elevation and the outer peripheral edge of the base, i.e., where the base meets the circumferential surface, is dimensioned such that the absorbent section of the test strip fits into this space. Moreover, the surface within this space can slope downwards to the edge of the base, so as to further promote the flow of the sample in the direction from the elevation down to the edge of the base.

In another refinement of the invention, the elevation comprises ridge-shaped elements that extend centrally from the elevation towards the base in order to convey the sample to the peripheral edge of the base of the container.

In this context, "ridge-shaped" is intended to signify any element that assists in the function of conveying the sample down from the elevation, in particular narrow, elongate elements fitted along the outer surface of the elevation, in the manner of ribs.

This measure has the advantage that the liquid sample is distributed in an improved and targeted manner about the peripheral edge of the base such that, if several test strips are arranged with their absorbent section at the peripheral edge, all the test strips are also supplied with a defined amount of sample.

In another refinement of the device according to the invention, the base of the container has a depression in the area of and extending around the circumferential surface, for the purpose of receiving the sample flowing down from the elevation.

This measure has the advantage that the saliva that flows down across the elevation, after the sampler has been squeezed out on the elevation, is collected and concentrated in a kind of groove or peripheral channel, such that the one or more test strips, which are arranged with their absorbent section in this depression or groove or channel, are supplied even more reliably with a sufficient amount of the liquid sample.

In another refinement, the at least one test strip, with its absorbent section taking up the sample, is adapted to the shape of the depression.

In this case, provision can be made, for example, that the absorbent section of the one or more test strips is bevelled with a wedge shape and is provided with its pointed end protruding into the depression. This measure has the advantage that the liquid sample can be transported in an even more concentrated form to the absorbent section, thereby ensuring a more reliable test procedure.

In another refinement of the device according to the invention, the sampling element, at its end remote from the end with the sampler, has a closure means for closing the container after the sampling element has been introduced into the container.

The closure ensures that the test can proceed without the sample being disturbed or affected. Moreover, this also ensures the safe transport of the device, for example to prepare the device for introduction into a reading appliance or scanner without any danger of the sample escaping from the container. The closure is advantageously at the same time the grip part of the sampling element, such that the latter can be securely held and safely handled via the closure. In this case, the sample of saliva is thus collected by inserting the other end of the sampling element, i.e., the end comprising the sampler, into the mouth or throat and by taking up/absorbing the saliva located therein into the sampler, while the sampling element is handled via the other end with the closure, which at the same time can be used as a grip, specifically either by the person who is to be tested or by another person.

In a refinement of the invention, the closure means is a press-fit, clip-on, rotary or bayonet-fit closure or a sealing ring which interacts in each case with the container and/or the holding element and/or an insertion element. It will be appreciated that the closure means can be constructed in one or more pieces, depending on the nature of the closure. It will also be appreciated that the closure means of the sampling element can interact with means provided on the corresponding parts of the container, in order to firmly close the container. Thus, the upper end of the container, i.e., the end that is intended to be closed, can have a mating thread, for example, in cases where the closure means of the sampling element has a threaded section.

In this case, the end of the sampling element may alternatively or additionally be provided with closure means which are inserted into the container, for example in the position in which the sampler is fixed on the rod-shaped section. These closure or fixing means on the sampling element can then interact with corresponding means in the holding element or in the container and/or with an insertion element for fixing the sampling element.

Moreover, it will be appreciated that, in addition to the closure means, a grip element can also be provided with which, for example in the case of a rotary closure, the sampling element can be taken hold of and screwed into the container.

In a refinement of the invention, the closure means is provided with means which, after the sampling element has been introduced into the container, block the removal of the sampling element from the container. In this case, it is particularly preferable if the means in question is a locking means that prevents the sampling element from being screwed out or pulled out after it has been introduced into the container.

Thus, by means of the closure piece, and by means of the container being closed by the closure piece, that is to say after introduction of the sample, for example the sample of saliva, it is ensured that the content of the container is not altered, in particular that the sample is not subsequently altered or adulterated. Moreover, this affords the possibility that the sample located in the container can also be used for further tests ("B-sample"). This means that the competent authority, or the person carrying out the test, can be assured that the sample present in the container is unadulterated, that is to say is in the state in which it was removed from the test subject. It can then be safely used for further tests.

In a preferred embodiment, the sampling element can therefore be constructed such that a closure section, for example a rotary closure section, is connected to what is by comparison a thinner, elongate, rod-shaped section, which in turn is connected by its other end to the absorbent sampler. The length of the sampling element is such that, when the element is introduced into the container and the container is closed, the absorbent sampler is either in a compressed state or in an uncompressed state, but the container as a whole is closed. In the compressed state, the user has to apply pressure to the sampler in order to close the container; in the uncompressed state, the sampler has to be first squeezed out in order to carry out the test, after which the container can then be closed without pressure being applied to the sampler.

In this connection and in a preferred refinement, the closure means has a pierceable, self-sealing element which, after it has been pierced, permits access to the interior of the container even after the closure means has been fitted onto the container.

This measure has the advantage that, when it is necessary to carry out further tests using the originally collected sample, it is possible to have simple and quick access to this original sample, specifically by a syringe or cannula or a similarly shaped and tapered sampling means being passed through the film-like element such that the latter is pierced, and the syringe/cannula/sampling means being used to remove some of the unused sample for further tests.

According to one embodiment of the device according to the invention, it is preferable if the container is a cylindrical container with a circular base.

In another embodiment, it is preferable if the container is a cuboid container with a rectangular base. This embodiment has the advantage that it can, for example, be read out by means of a scanner, since the planar sides of the container make uniform reading possible.

Irrespective of the specific shape of the base and the circumferential surface, a shape of the holding element that is adapted "to the shape of the circumferential surface" should be understood as meaning that the shape of the holding element or the holding element is adapted peripherally to the shape of the circumferential surface forming the inner side of the container such that that it covers the entire peripheral inner circumference of the circumferential surface. This means that, if the circumferential surface is designed as a—hollow—cylinder, in particular a circular or angular cylinder, the holding element is also designed as cylindrical, in particular circular-cylindrical or angular-cylindrical. It will be appreciated that the holding element does not necessarily also cover the entire height of the cylinder. Accordingly, the holding element is designed as a hollow cylinder which is adapted to the inner cylindrical shape of the circumferential surface.

It is also preferable if the holding element bears at least partially on the inner face of the circumferential surface of the container. The bearing of the holding element on the inner face of the circumferential surface thus prevents direct contact between the liquid sample and that part of the test strip that contains the reagents. In this way, only that part of the test strip not containing any reagents comes into direct contact with the liquid sample. Some of the sample is then drawn by capillary forces in the longitudinal direction of the test strips and into the area of the reagents. This prevents contamination of the liquid sample, which is why the sample can be sent to a laboratory for further tests without taking out the test strips.

It is also preferable if the holding element is at least partially spaced apart from the inner face of the circumferential surface of the container. The spacing apart of the holding element is advantageous, since this facilitates contact between the sample to be tested and the test strips.

According to another embodiment, the holding element is shaped with pretensioning and clamped into the container. The pretensioning of the holding element permits a good clamp fit within the container and prevents slipping of the holding element and of the test strips arranged therein. This is in turn important for preventing contamination of the sample by the reagents arranged on the test strips.

In another preferred embodiment, the holding element is at least partially bonded to the container, in particular to the inner face of the circumferential surface and/or of the base. Like the abovementioned clamp fit, the bonding of the holding element to the container can prevent slipping of the holding element and thus prevent contamination of the sample.

It will be appreciated that this bonding can also be used in combination with the clamp fit, thus additionally improving the connection between holding element and container.

As an alternative to this, it is possible for the holding element to be fitted through a guide means arranged on the base of the container. A guide means on the base of the container has the advantage that the holding element can be inserted more easily and thus more quickly into the container during production.

Moreover, in a preferred refinement, the holding element has recesses in which the test strips are respectively arranged. The recesses allow the test strips to be fitted in place and prevent slipping of the test strips inside the holding element, that is to say in the longitudinal direction of the test strips.

It is also preferable in this case if the recesses are separated by webs, which bear at least partially on the inner face of the circumferential surface of the container. The separation by webs arranged between the individual test strips prevents contact between the reagents of the various test strips. In addition, the webs can prevent the liquid sample from getting into that area of the test strips where the reagents are arranged, such that the liquid sample can reach only the lower free end of the test strips where there are no reagents present. This therefore prevents contamination of the sample itself and ensures that the individual test strips and their reagents do not influence one another.

In the aforementioned device, it is also preferable if at least part of the circumferential surface of the container has a transparent area in the region of the test strips. It is thus possible to ensure that there is a direct optimal view of the test strips and that the result can be read off without removing the holding unit.

In another embodiment, it is preferable if the holding element has a darker colour compared to the test strips.

This measure has the advantage of making it much easier to read off the test result on the test strip, since the contrast between the then brighter test strip and the holding element is greater than if the holding element is the same colour as or brighter than the at least one test strip.

The liquid sample to be tested can be any liquid sample of a body fluid from a human- or mammal in general—preferably saliva.

It is also preferable if the transparent area is concealed by an at least partially detachable covering element, in particular by a film that cannot be seen through. The covering element affords the advantage of preventing the test results from being read off by the subject or by other unauthorized persons.

In another preferred embodiment, the size of the covering element is chosen such that the area of the circumferential surface adjacent to the base is not concealed by the covering element. Through the uncovered area remaining at the lower end of the circumferential surface, the person carrying out the test can identify directly whether the liquid sample to be tested is present in the container in a sufficiently large quantity to permit contact with the test strips.

According to another preferred embodiment, a cover element, in particular a protective film, covers the test strips arranged in the recesses of the holding element. The covering of the test strips, particularly in the area containing the reagents, is advantageous since it prevents direct contact between the liquid sample and the reagents present on the test strips. The liquid sample thus comes into contact with the test strips only at the lower part of the test strips, where there are no reagents present. Some of the liquid sample is then drawn by capillary forces into the area of the reagents. This in turn prevents contamination of the sample.

The device according to the invention can have between 1 and 12 test strips, in particular, 1, 2, 3, 4, 5, 6, 7, 8, 9, 10, 11 or 12 test strips, which can each be used after insertion into the holding element. It is particularly preferable for the device to have at least six test strips.

In a further embodiment it is preferred if an insertion element by means of which the sampling element can be inserted into the container is additionally provided. The insertion element preferably has a hollow, substantially cylindrical shape, with an upper end, opposite from the base of the container, and a lower opening, facing the base. The sampling element may be inserted into this insertion element via the upper end thereof, and reaches through the lower opening into the container, and can as a result be squeezed out on the elevation provided on the base. It will be appreciated that the insertion element is either already inserted in the container—and as a result also in the holding element present therein—and only then is the sampling element inserted, or on the other hand the sampling element may have already been brought together with the insertion element before insertion into the container, and this assembled arrangement is inserted into the container.

The insertion element offers the advantage that additional fixing of the sampling element is made possible. In a preferred embodiment, the insertion element may also have at the upper end two lateral flanges, which limit insertion of the insertion element by the flanges lying on the upper edge of the container.

In a further embodiment it is preferred if the base of the container has means by which the sample of body fluid can be conveyed from the elevation to the side edges of the base, in particular the long side edges in the case of a rectangular base. This ensures that the sample of body fluid is conveyed from the elevation to the region into which the absorbent sections of the test strips protrude, and so starting of the test is ensured after the squeezing out. In a preferred embodiment, these means are elevations which are provided at a distance from the elevation on which the sampler is squeezed out and in each case adjacent to the short side edges of the base.

Irrespective of the particular embodiment, the device according to the invention can be used for any type of test for a drug or for multiple drugs. The sample of liquid can be tested at one and the same time for several drugs of abuse, including in particular amphetamines, barbiturates, benzodiazepines, cocaine, marihuana, methadone, methamphetamine, methylenedioxy-methamphetamine, morphine, opiates, oxycodone, phencyclidine, propoxyphene, tricyclic antidepressants, buprenorphine, cotinine, EDDP (2-ethylidene-1,5-dimethyl-3,3-diphenylpyrrolidine) and fentanyl.

The analytes, in particular drugs, are preferably detected using an immunoassay based on the principle of competitive binding. For this purpose, the test strip contains, for example on a test line, a membrane, for example a nitrocellulose membrane, coated with analyte (in particular drug)-protein conjugates (for example pure bovine serum albumin) and, on a control line, a polyclonal antibody (goat) against gold protein conjugate and a colour field with gold particles that are coated with specific monoclonal antibodies for the drugs to be detected and are immobilized in the test field. If drugs are present in the liquid sample, these compete with their conjugates for binding sites on their specific antibody. During the test, the sample, for example, urine or saliva, migrates "upwards" by capillary forces, i.e., from the sample-receiving end of the test strip to the upper end of the test strip. The drug-protein conjugates on the test strip go into solution and migrate with the sample to the test area of the corresponding drug detection strip. Drugs that are contained in concentrations below the detection limit in the liquid sample, particularly saliva, do not saturate the binding sites of their specific antibodies immobilized in the test field, such that the antibodies in this case react with the conjugates, as a result of which a coloured line becomes visible. If the concentration of the drugs in the urine or the liquid sample is higher, the drug molecules drive the conjugates from the urine or occupy all the antibody binding sites, as a result of which no coloured line is formed.

To check whether the test has been performed correctly, i.e., whether the test strips are working properly, for example, or whether a sufficient amount of the sample has been taken up by the test strips, the test strips can have a control area in which a coloured line appears each time the test is carried out, independently of any drugs possibly present in the urine or the liquid sample.

In a preferred embodiment, the following detection limits are provided for certain drugs: amphetamine: ca. 50 ng/ml and upwards; cocaine: 20 ng/ml and upwards; marihuana (tetrahydrocannabinol): ca. 20 ng/ml and upwards; methamphetamine 50 ng/ml and upwards; methylenedioxymethamphetamine: ca. 50 ng/ml and upwards; opiates: 40 ng/ml and upwards; phencyclidine: ca. 10 ng/ml and upwards.

The test strips can be designed in one or more pieces. In the present context, "one or more pieces" means that the test strip can be formed in one section or from several interconnected, for example overlapping, parts which can be made of different or identical materials with different or identical dimensions.

It will also be appreciated that one or more analytes, preferably two analytes, can be detected on one or more test strips, that in addition control zones can also be provided for confirming that the test has been carried out completely and correctly, and that the strips can be preceded by samplers that serve, for example, to take up and forward the sample. All of these features are known to persons skilled in the art and represent routine technical features belonging to the general technical knowledge in this field. In this respect, reference is also made explicitly to the disclosures of the aforementioned documents EP 0 225 054, EP 0 183 442, EP 0 186 799, EP 0 299 359 and WO 89/06799, which list a number of analytes to be detected and also a number of samples.

According to a further embodiment, it is also preferable if the test strips include an alcohol test. The alcohol test makes it possible not only to test the sample for illegal drugs of abuse or other analytes, but also to combine this with detection of the alcohol content of the sample. In police checks in particular, this embodiment can thus provide a quick and simple indication that the subject is unfit to drive.

In a preferred embodiment, an alcohol content of at least ca. 0.04% is detected. It is preferable if the detection takes place by a reaction of the enzymes alcohol oxidase, peroxidase and an enzyme substrate, for example tetramethylbenzidine, in the presence of ethanol.

With the test strip for detection of alcohol, it is advantageously only the actual presence of alcohol that is detected. However, other measures can be taken in order also to determine the amount of alcohol present in the sample, for example a reaction providing a colour intensity which differs in intensity, in particular with an increasing alcohol content, and which can be read off on the basis of a scale that is also supplied.

Moreover, in another embodiment, it is preferable if the device comprises at least one test strip for detecting adulteration of the sample.

It is particularly preferable in this case if the test strips for the adulteration tests include a colour reaction, which is then compared with colour fields on a colour scale. These colour scales can be supplied together with the device, such that the user himself can directly test for/detect adulteration. It is particularly preferable if the colour reaction is classed as "normal" (unadulterated sample) and "abnormal" (adulterated sample).

It is also preferable that the container is a cylindrical container with a circular base and that the holding element has a curved shape adapted to the circular cross section of the circumferential surface. The container is thus a round beaker, thus facilitating the insertion of the holding element and, later, the reading off of the test results. The cylindrical container can preferably have a diameter of ca. 1 cm to ca. 15 cm, preferably of between ca. 1 cm and 5 cm.

It will be appreciated that the aforementioned features and those still to be explained below can be used not only in the respectively cited combination but also in other combinations or singly, without departing from the scope of the present invention.

BRIEF DESCRIPTION OF THE DRAWINGS

Exemplary embodiments of the invention are explained in more detail in the following description and are illustrated in the drawing, in which:

FIG. 1A shows a schematic view of the individual elements of an embodiment of the device according to the invention, in the unassembled state, which device is used to test samples of body fluids.

FIG. 1B illustrates a container portion in accord with embodiments of the invention.

FIG. 1C illustrates an insert portion in accord with embodiments of the invention.

FIG. 2A shows a schematic view of the elements from FIG. 1 in the assembled state, without a covering.

FIG. 2B shows a view as in FIG. 2, with partial covering of the test strips and containers.

DESCRIPTION OF PREFERRED EMBODIMENTS

Figure 3:
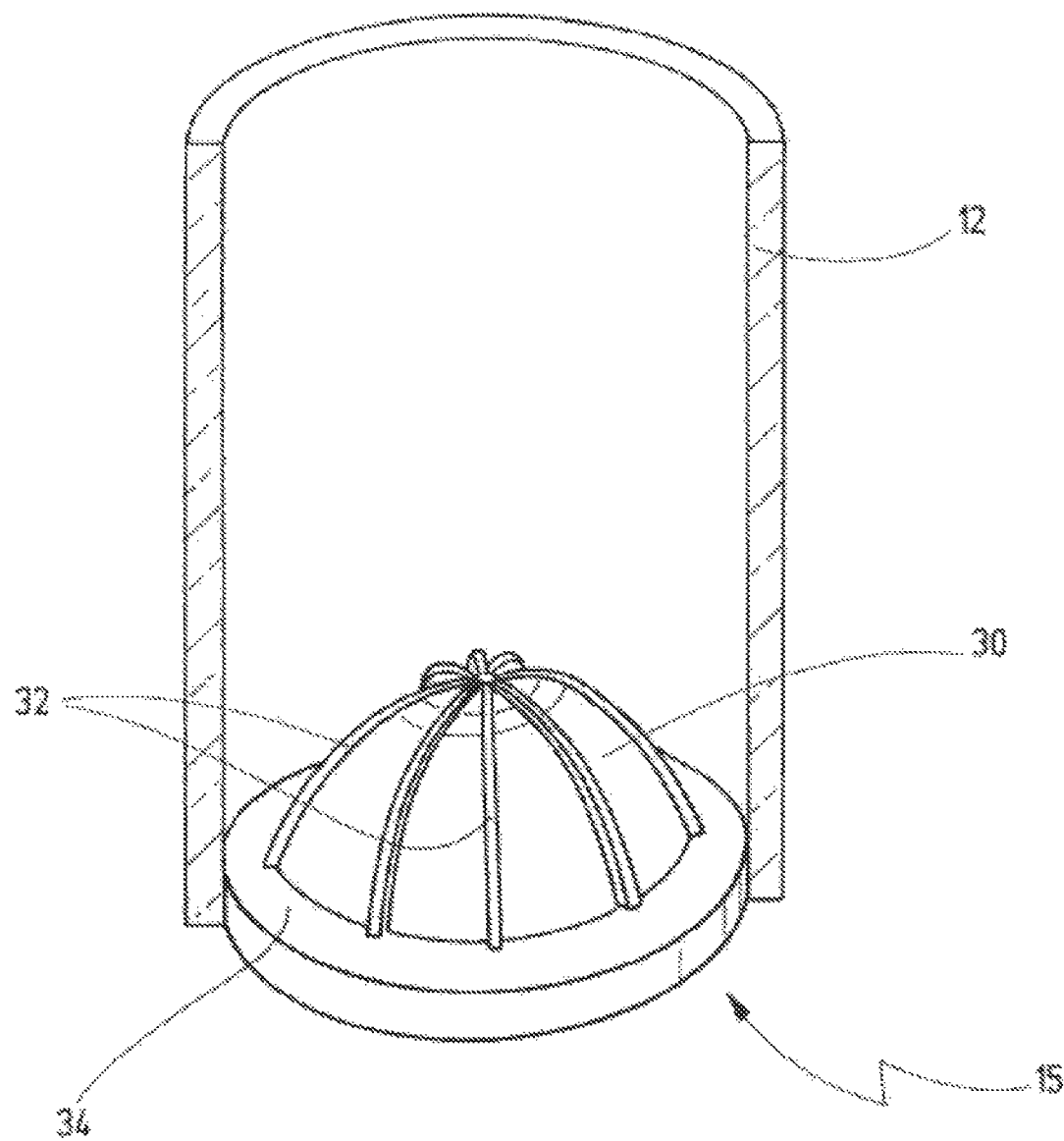
FIG. 3 shows an enlarged perspective view of an embodiment of the base of the container of the embodiment shown in FIGS. 1 and 2.

An embodiment of a device 10 according to the invention for testing samples of liquid is shown in FIG. 1, where the individual elements of the device 10 are depicted, and the device 10 as a whole is in the unassembled state.

The device 10 comprises a container 12, and a holding element 13 which is to be arranged in the container 12 and which holds one or, as is shown in FIG. 1, several test strips 18. The test strips 18 have absorbent sections 19 via which the liquid sample is taken up and the test is thereby started on the test strip 18.

In the embodiment shown in FIG. 1, the container 12 is cylindrical with a circular base 15 and with a roundly curved circumferential surface 16. The container 12 also comprises, at its upper end, a thread 17 which, by engagement with corresponding means, serves to close the container 12.

The holding element 13 has lengthwise axial recesses 14a, which are separated from one another by webs 14b lying between the recesses 14a. The recesses 14a and the webs 14b are delimited at the top by a free surface of the holding element 13. However, the recesses 14a of the holding element 13 continue as far as the bottom end thereof. In FIG. 1, test strips 18 are inserted in the recesses 14a of the holding element 13. In this embodiment, the test strips 18 are inserted with an exact fit into the recesses 14 of the holding element 13 and are separated from one another by the webs 15. The test strip 18 is divided into a section 18a, in which the test results can be read off, and a section 18b, on which the name of the analyte that is to be tested is marked. The section 18a thus comprises the reagents which, by reacting with the analytes to be tested, are responsible for indicating a test result. The fact that the shape of the holding element 13 matches the circumferential surface 16, extending in the example shown in FIG. 1 peripherally over the entire inner circumference of the circumferential surface 16, means that the results can be read off very easily by sight. Moreover, the test strips 18 also have absorbent sections 19 via which the sample is taken up onto the test strip 18.

FIG. 1 also shows the sampling element 20. The latter comprises, at its end to be inserted into the container 12, a sampler 22 with which, for example, a sample of saliva can be taken from the mouth or throat. The sampler 22 has a structure similar to cotton wool or sponge or is made of a material that is able to absorb and store liquid. An elongate, rod-shaped section 23 connects the sampler 22 to the end section 24 which, in the embodiment shown in FIG. 1, also comprises the grip 25 and the closure means 26. The closure means 26 shown in FIG. 1 is a rotary closure means, that is to say a thread which is provided on the end section and which, when the sampler 22 is inserted into the container 12, engages with the mating thread 17 of the container 12.

The elements of the embodiment of the device according to the invention shown in FIG. 1 are shown in the assembled state in FIG. 2A. It will be seen from FIG. 2 that the holding element 13 is inserted into the container 12 such that the absorbent sections 19 of the test strips 18 located in the holding element 13 are in contact with the base 15 of the container 12. The sampling element 20 is also introduced into the container 12 in such a way that the sampler 22 is inserted into the container 12, and the closure means 26 engages with the mating thread 17 of the container 12 in order to close the container 12.

FIG. 2B shows the same embodiment as in FIG. 2A, with the additional feature of a partial covering element 27 of the test strips 18. This covering element 27 is applied, for example by adhesive bonding, to the outer surface of the container 12, specifically below the area 18a, that is to say the area where the test results are indicated. The covering element 27 can, for example, carry instructions on how the test results are to be evaluated, for example to the effect that, if a band appears in the area 18a of the test strip 18, the subject has tested positive to a specific analyte ("pos"), or, if two bands appear in the area 18a, the subject is negative ("neg") with respect to the analyte, and, if no band can be seen in the area 18a, the test is invalid ("invalid").

At the lower edge adjacent to the base 15, the circumferential surface 16 of the container 12 can have a section 28 not covered by the covering element 27. This uncovered section 28 offers the possibility, for example, of checking whether the liquid sample to be tested is present in a sufficient quantity.

As has already been explained above, the holding element 13 can be darker compared to the colour of the test strips 18, which makes the test result easier to read off in the area 18a, since the darker colouring makes the contrast to the test strip greater than would be the case with a brighter coloured holding element 13.

It will be appreciated that the whole container 12 can also be provided on its outer surface with a covering element and that in the area 18a, i.e., where the test result is read off, there is an area in which the covering element can be detached from the container such that the test result and the area 18a of the test strips can be seen from the outside. The covering element can, for example, be adhesively bonded to the outer surface of the container, the adhesive selected for the area that is to be detached, to allow the test results to be read off, being a more easily releasable adhesive than the one selected for the areas that remain on the surface of the container.

FIG. 3 shows an enlarged view of the internal design of the base 15 of the container 12, the side wall of the container 12 having been cut away to show the design of the base. It will be seen from FIG. 3 that the base 15 has an elevation 30 in the form of an opened hemisphere, the latter being arranged centrally on the base 15, with its curvature pointing in the direction of the other end of the container 12. The elevation 30 also comprises ridge-shaped elements 32 which, starting from the highest point of the elevation 30, are routed down the sides thereof. The base 15 further comprises a depression or sample-collecting channel 34 which is formed all round the edge to the circumferential surface and which collects the sample running down from the elevation 30 and guided from the latter by the ridge-shaped elements 32. The absorbent sections 19 of the test strips 18 are received in this depression or sample-collecting channel 34, such that the sample located in the sample-collecting channel 34 can be taken up by the absorbent sections 19 into the test strips 18 by capillary forces, and the test for determining the analyte or analytes can proceed on the one or more test strips 18.

Figure 4:
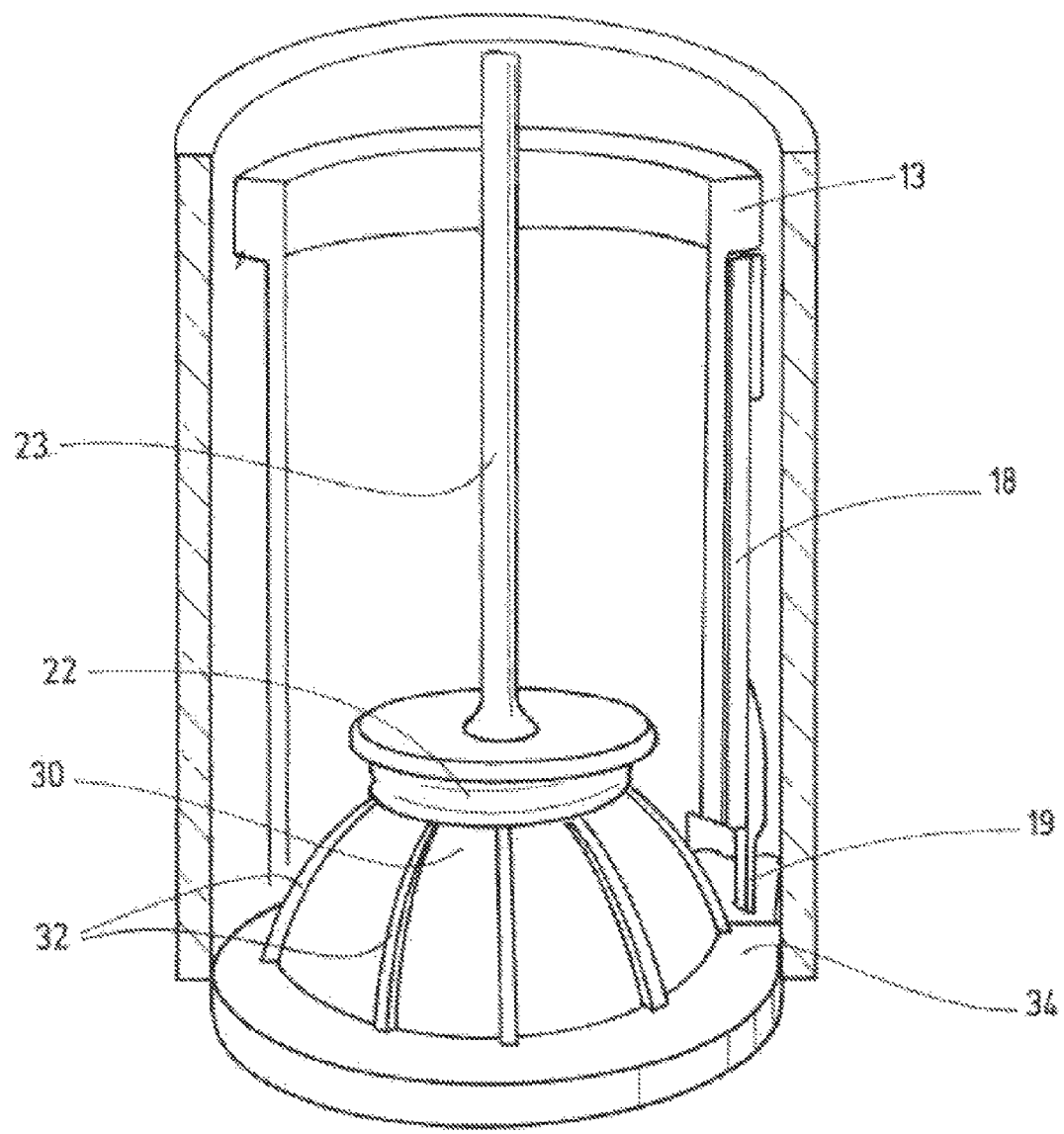
FIG. 4 shows a detail of the lower section of the container comprising the base of the embodiment shown in FIG. 3, with the sampling element inserted into the container, and with the sampler in the compressed state on the elevation.

FIG. 4 shows a view in which the end of the sampling element 20 comprising the sampler 22 is pressed onto the elevation 30 of the base 15 of the container 12. The sample that has been taken up by the sampler 22 and stored therein is thus squeezed out on the elevation 30 and runs down the side of the latter into the sample-collecting channel 34. The flow of the sample down from the elevation is additionally promoted by the ridge-shaped elements 32 provided on the elevation 30, and these elements 32 aid the uniform distribution of the sample in the circumferential sample-collecting channel 34.

It will also be seen from FIG. 4 that the test strip 18 introduced into the holding element 13 protrudes with its absorbent end 19 into the sample-collecting channel 34.

Figure 5:
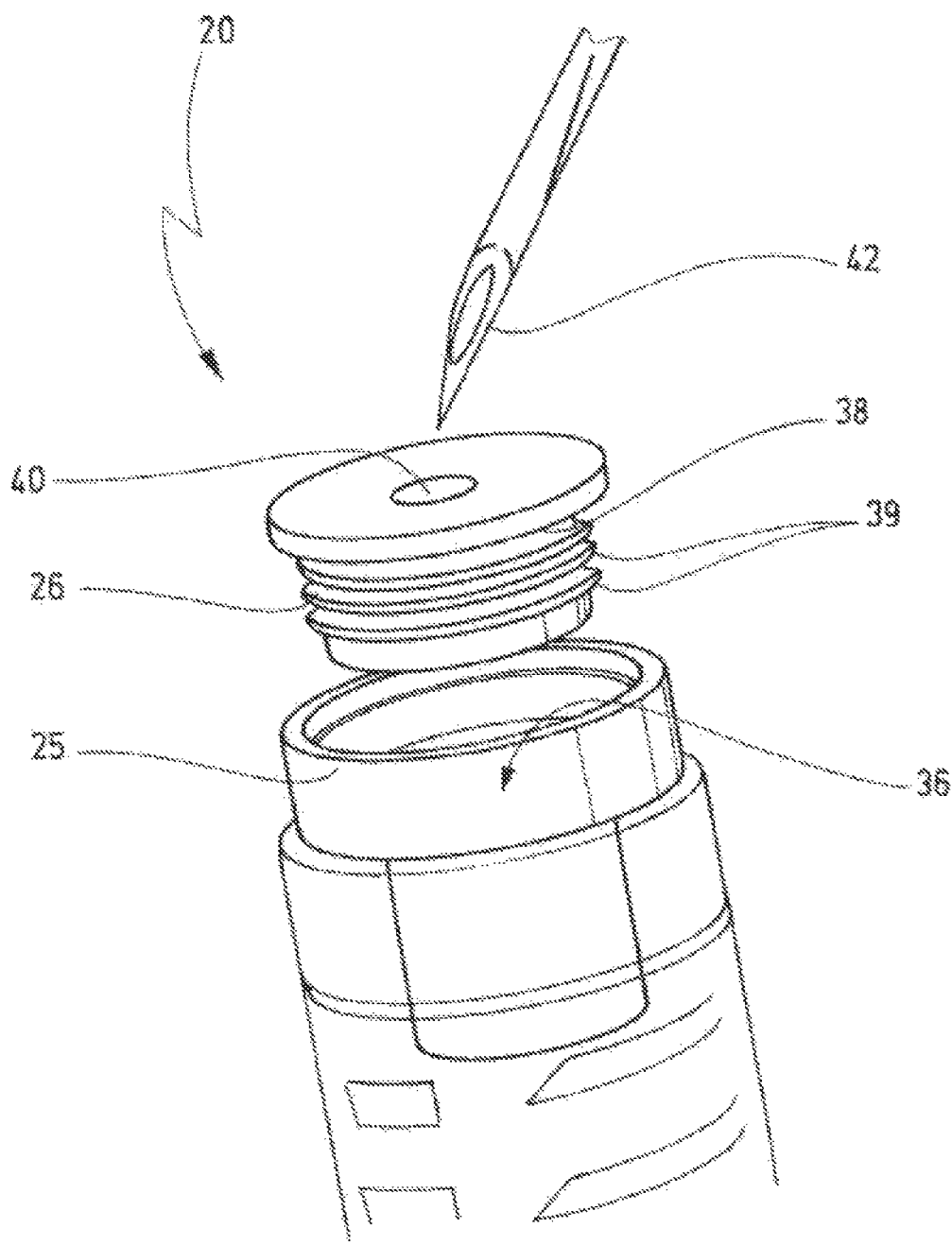
FIG. 5 shows a detail of the upper section, comprising the grip and the closure means, in one embodiment of the sampling element.

FIG. 5 shows in detail an embodiment of the end of the sampling element 20 that comprises the grip 25 and/or the closure means 26. A B-sample container 36 is provided centrally in the head of the sampling element 20 and has a closure cap 38 that is to be firmly closed and that cannot be opened again without this leaving a sign that it has been opened. The closure cap 38 has closure lamellae 39 extending around its side, and a self-sealing, pierceable sampling element 40 via which, for example, material for the B-sample can be removed using a syringe or cannula, as is shown schematically by the partially depicted syringe tip 42.

Figure 6:
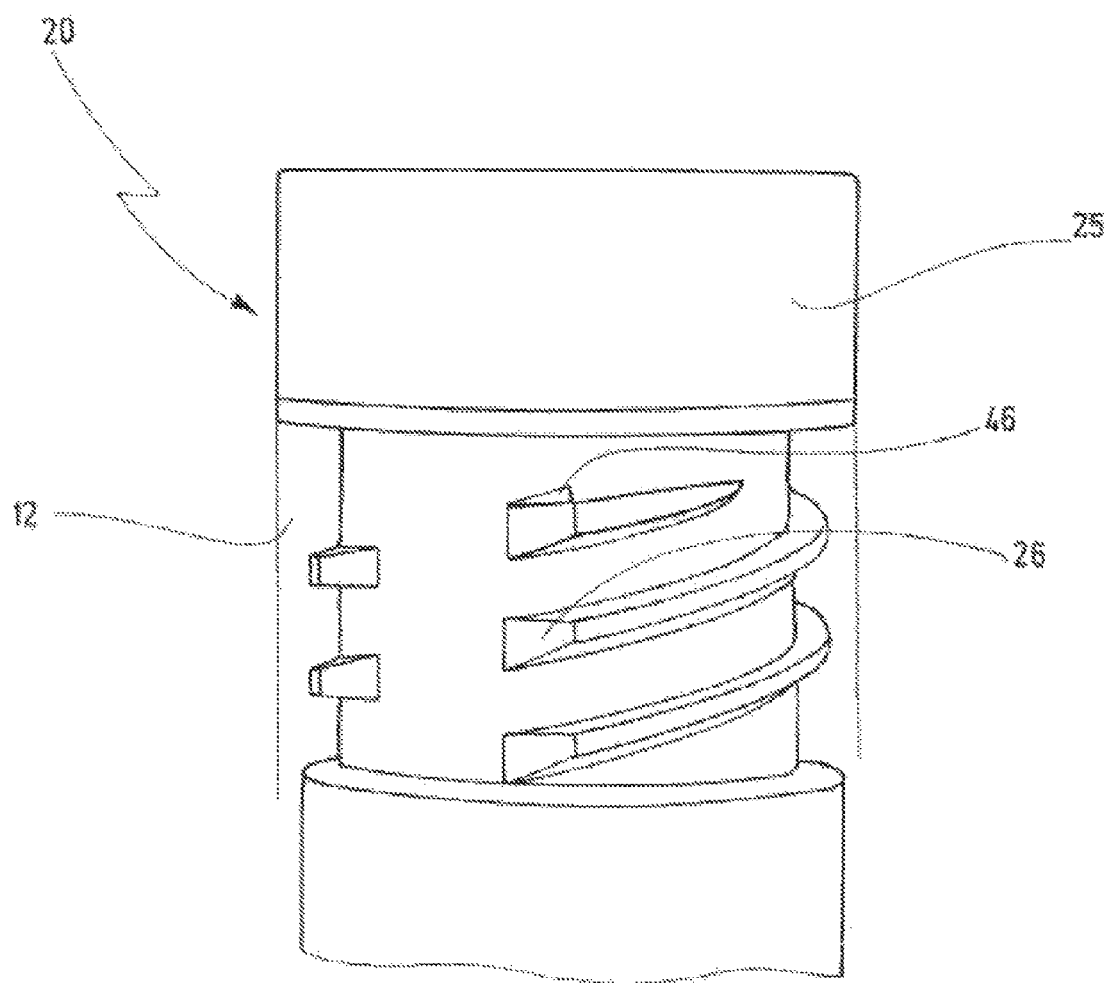
FIG. 6 shows a detail of an embodiment of the closure means, in engagement with means that are correspondingly provided in the container and are used to close the device.

FIG. 6, finally, shows an enlarged view of the end of the sampling element 20 comprising the closure means 26. The outermost end section forms a kind of grip 25, and the closure means 26 are designed in the form of a thread, which engages in a mating thread 17 provided on the container 12. The mating threaded piece designated by 44 in FIG. 6 has a catch 46 which, when actuated, secures the mating thread 17. The catch 46 can be made particularly noticeable by a corresponding marking or a corresponding indicator on the outer container, in order to indicate the possibility of monitoring.

Figure 7:
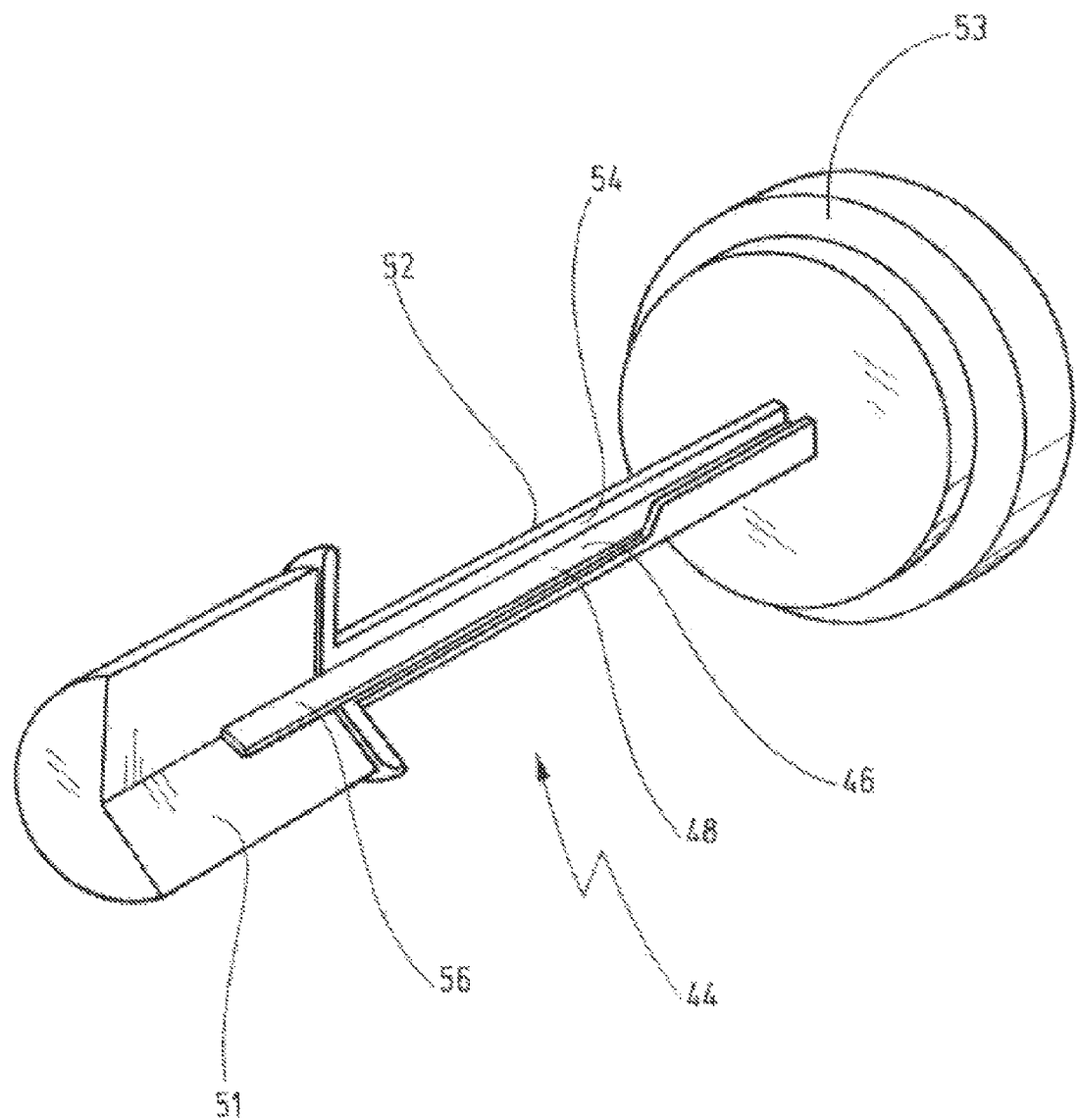
FIG. 7 shows a detailed plan view of the sampling element of an embodiment of the device according to the invention with means for indicating a sufficient amount of liquid sample in the sampler.

FIG. 7 shows a detailed view of a further embodiment of a sampling element 44 of the device 10 according to the invention. The sampling element 44 likewise has a sampler 51, a rod-shaped section 52 and a grip 53. The rod-shaped section 52 also has a U-shaped recess 54—seen in cross section—in which an indicator strip 46 for indicating the presence of an amount of liquid sample sufficient for carrying out the assay is inserted. The indicator strip 46 protrudes with one of its ends 47 into the sampler 51, making it possible for liquid sample that is taken up by the sampler 51 to get into the indicator strip 46 of an absorbent material. The liquid sample then migrates through the indicator strip 46 as far as a specific zone 48 of the indicator strip 46 that lies at a specific distance away from the sampler 51 in the rod-shaped section 52 of the sampling element 44, and by means of which zone 48 it can be established that a sufficient amount of liquid sample is present in the sampler 51. This zone 48 may be provided with specific indicating means by which it can be established, for example by means of a colour reaction, when the liquid sample enters the zone 48 that there is sufficient sample to be able to carry out the assay.

In a further embodiment, it may be provided that the rod-shaped section 52 of the sampling element 44 has a marking, for example at the level of the zone 48, which indicates the minimum travelling distance of the liquid sample on/through the indicator strip. The marking may be, for example, a line or a notch in the rod-shaped section 52.

Figure 8A:
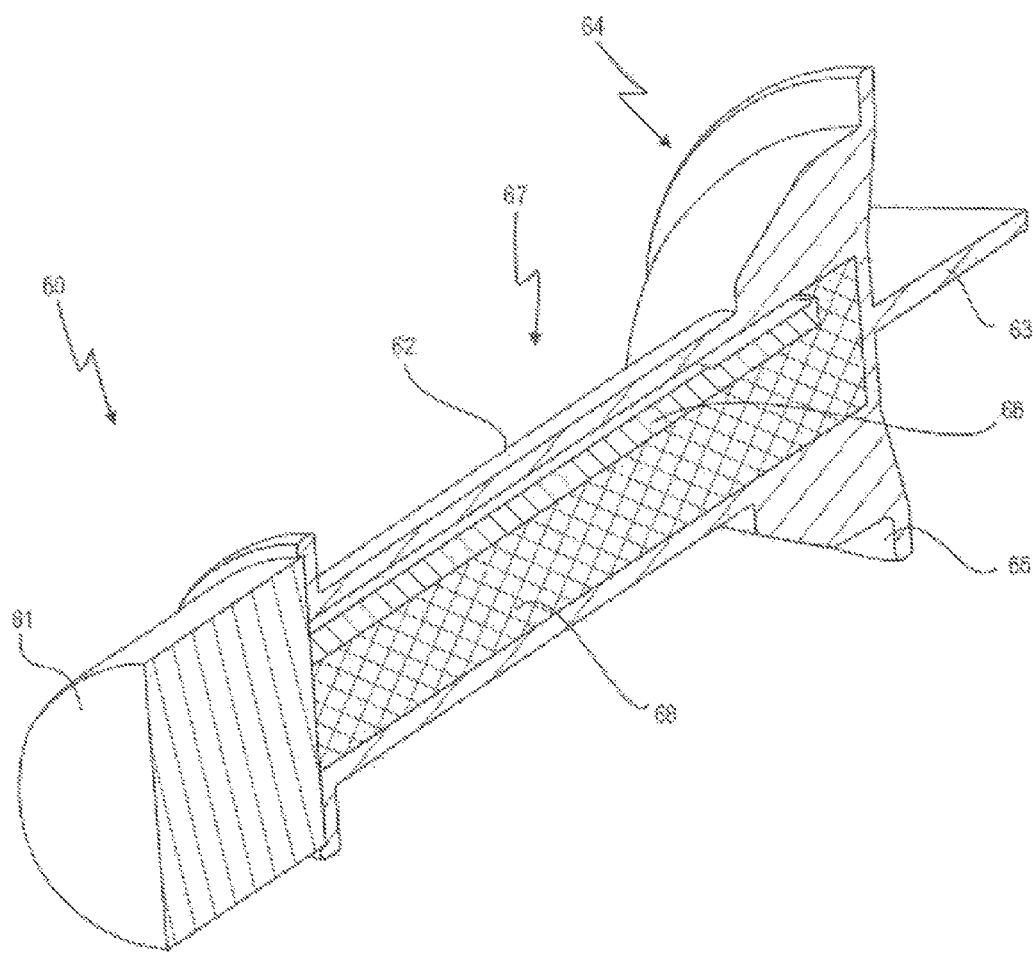
FIG. 8 shows a further embodiment of a sampling element, in longitudinal section (A) and in an exploded representation (B).
Figure 8B:
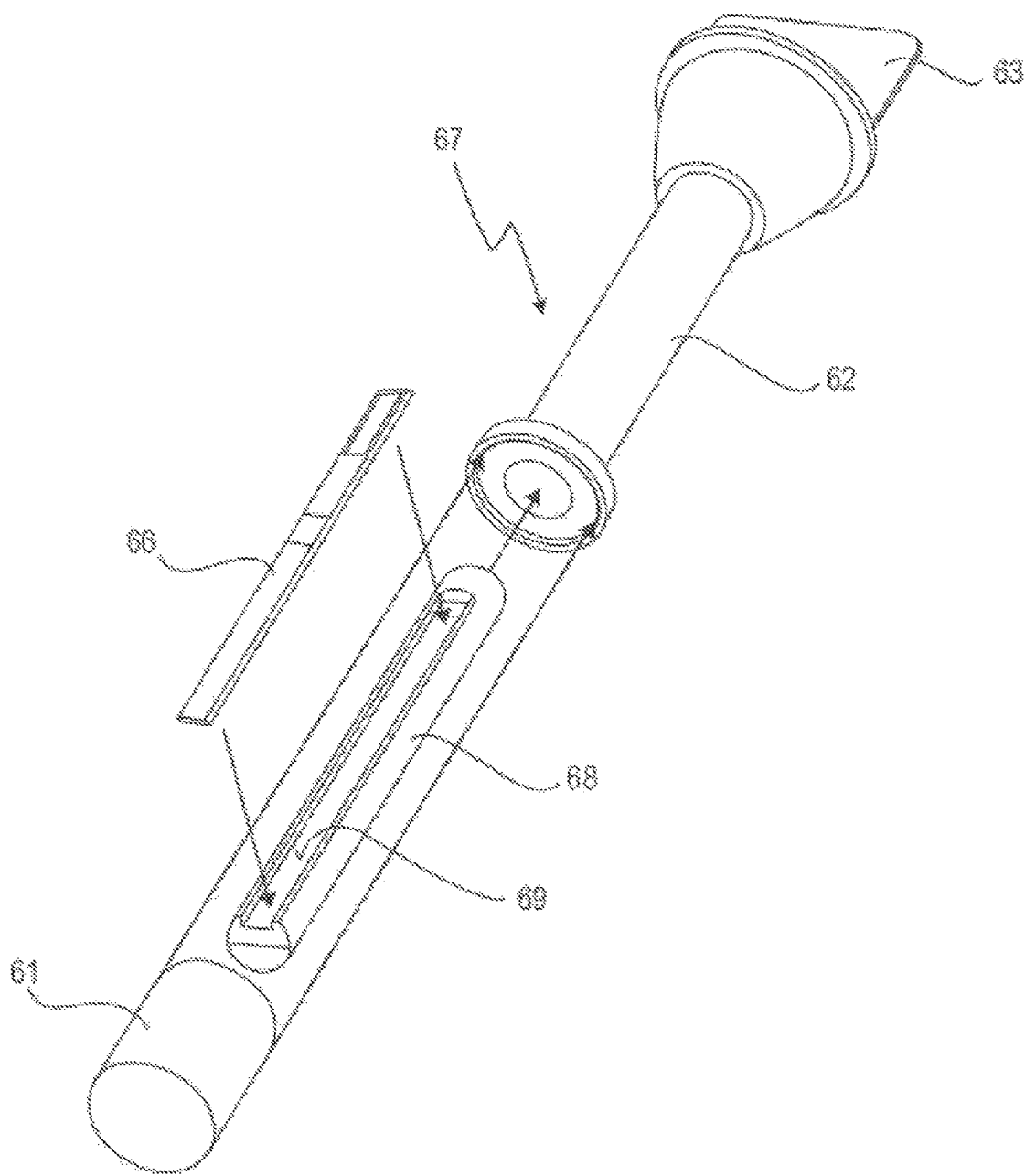

A further embodiment of the sampling element 60 is shown in FIG. 8, FIG. 8A showing a longitudinal section through the sampling element 60, and FIG. 8B showing an exploded representation of the individual parts or sections of the sampling element 60. In the embodiment shown in FIG. 8, said sampling element likewise has a sampler 61, as well as an elongate, rod-shaped section 62 and an end section 64, which comprises a grip 63 and closure means 65. The elongate, rod-shaped section 61, and the end section 64 including the grip 63 and the closure means 65, are formed in one piece in the embodiment shown in FIG. 8, in the form of a hollow rod 67 with a holding grip, which can be seen in particular in FIG. 8B. The sampler 61, a sponge-like element, is fastened to the end of the rod 67 that is to be inserted into the container 12. An insertion element 68, which has a U-shaped recess 69—seen in cross section—into which an indicator strip 66 can be inserted or placed, can be inserted into the rod 67. The rod 67 is in this case produced from a transparent material, so that, after insertion of the insertion element 68 and the indicator strip 66 lying therein into the hollow rod 67, it can be read off from the indicator strip whether and when sufficient liquid sample has been taken up by means of the sampler 61.

Figure 9A:
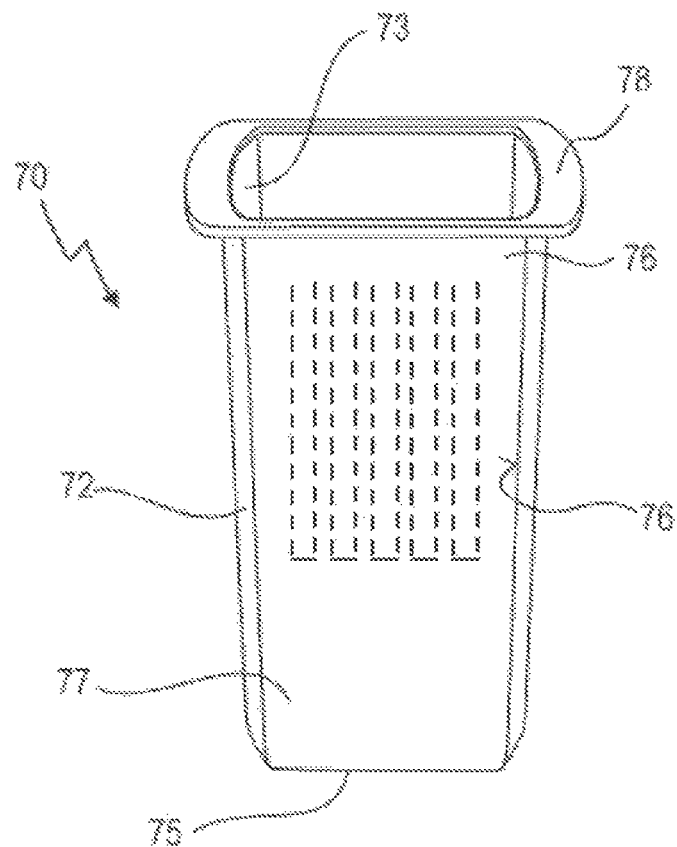
FIG. 9 shows a further embodiment of the device according to the invention, the partially assembled form being shown in (A); the holding element removed from the container being shown in (B); the sampling element being shown in (C) and an insertion element for the sampling element being shown in (D).
Figure 9B:
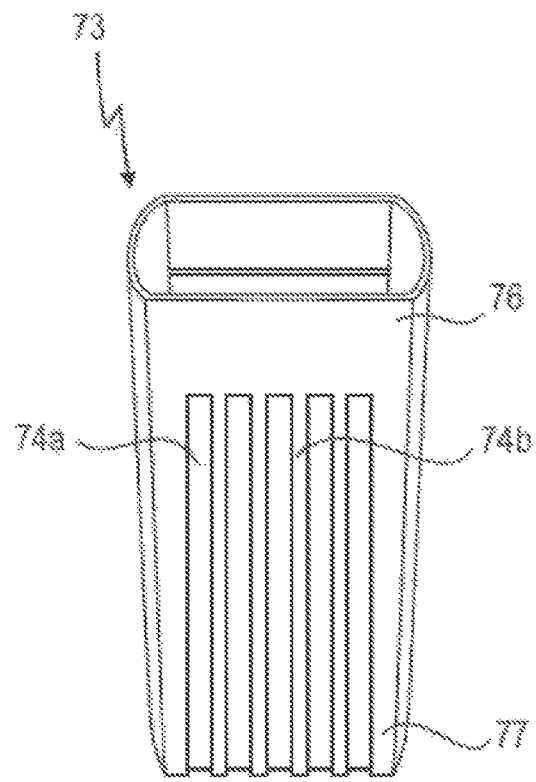

A further embodiment of the device 70 according to the invention or parts thereof is shown in FIG. 9, with a container 72 and a holding element 73 arranged therein (FIG. 9A), which is also shown separately in FIG. 9B. As can be seen from FIGS. 9A and 9B, the holding element 73 has a hollow angular-cylindrical shape, which is adapted to an inner circumferential surface 76 of the container 72, so that the holding element 73 can be inserted into the container 72 such that it fits. The base 75 of the device 70 is of a substantially rectangular design, corresponding to the circular-cylindrical shape of the circumferential surface 76. The holding element 73 has recesses 74a and webs 74b lying between the recesses 74a, both being delimited in a top section of the holding element 73 that is facing the open end of the container 72, and formed continuously as far as the end that in the inserted state is facing the base 75 of the container 72. Test strips, which are not shown in FIG. 9 for reasons of clarity, may be inserted in the recesses 74a. In the inserted state, the lower end 77 of the holding element 73 facing the base 75 of the container 72 ends at a specific distance from the base 75, so that the test strips present in the recesses 74a protrude with an absorbent section out of the holding element 73 and the recesses 74a such that that they come into contact with the liquid sample that is preferably present between the base 75 at the lower end 77 of the holding element 73, or are immersed in the sample.

The end 77 of the holding element also has centrally a holding element opening 76 (see FIG. 10), which is dimensioned such that the sampling element 80 can be guided with its sampler 82 through the holding element opening 76 to the elevation (not shown in FIG. 9) present on the base 75 and squeezed out on it. The holding element opening 76 is preferably substantially round or adapted for receiving and leading through the lower end 94 of the insertion element 90.

Figure 9C:
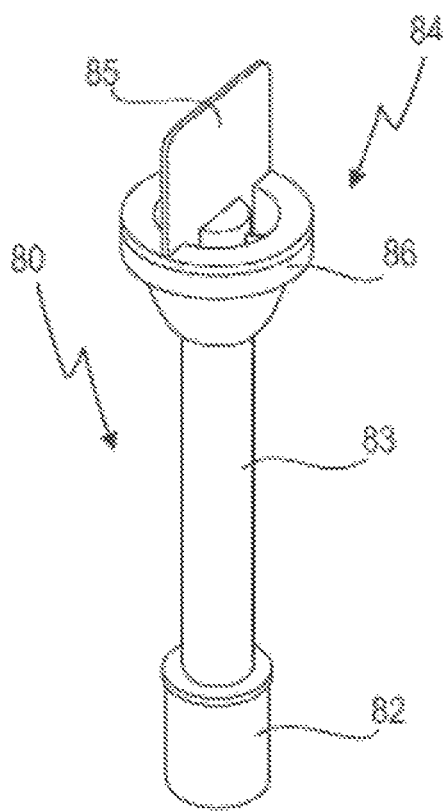

Shown in FIG. 9C is an embodiment of the sampling element 80 which can be used in the case of the embodiment of the device 70 shown in FIG. 9 and which corresponds substantially to the embodiment of the sampling element shown in FIG. 8A and FIG. 8B. Accordingly, the sampling element 80 has a sampler 82, an absorbent, sponge-like element by means of which the sample is taken up, as well as a rod-shaped section 83, and an end section 84, which in turn has a grip 85 and closure means 86. In the embodiment shown in FIG. 9C, the closure means are a peripheral sealing ring which interacts with an opening 92 in an insertion element 90 that is represented in FIG. 9D when the sampling element 80 is inserted into the opening 92 in the insertion element 90. The sealing ring engages in the opening 92 in a sealing manner, so that slipping of the sampling element 80 out of the insertion element 90 is avoided.

Figure 9D:
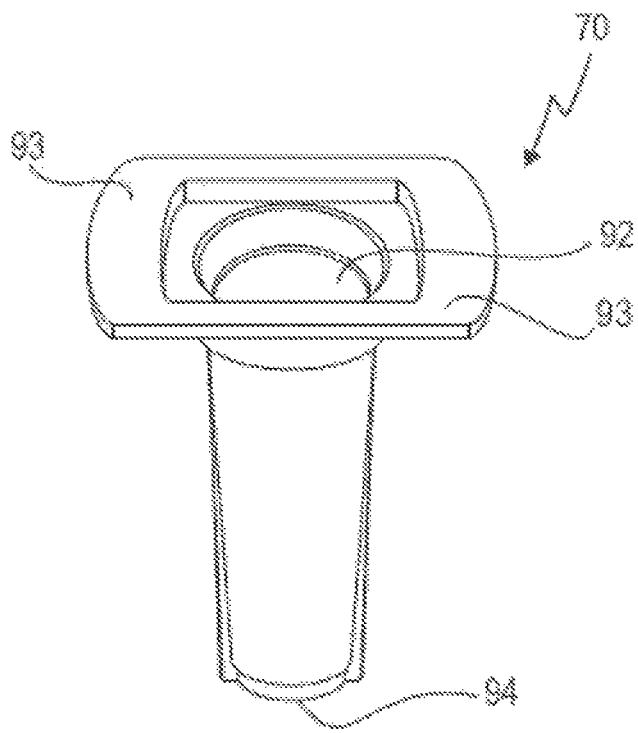

The insertion element 90 shown in more detail in FIG. 9D has a substantially hollow cylindrical shape, with an opening 92 at the end by which the sampling element 80 is inserted, and with an open end 94, from which the sampler 82 is at least partially led out in the direction of the base 75 of the container 72 and, as a result, can be pressed onto an elevation (not shown in FIG. 9) provided on the base 75 of the container 72 and squeezed out.

Figure 10:
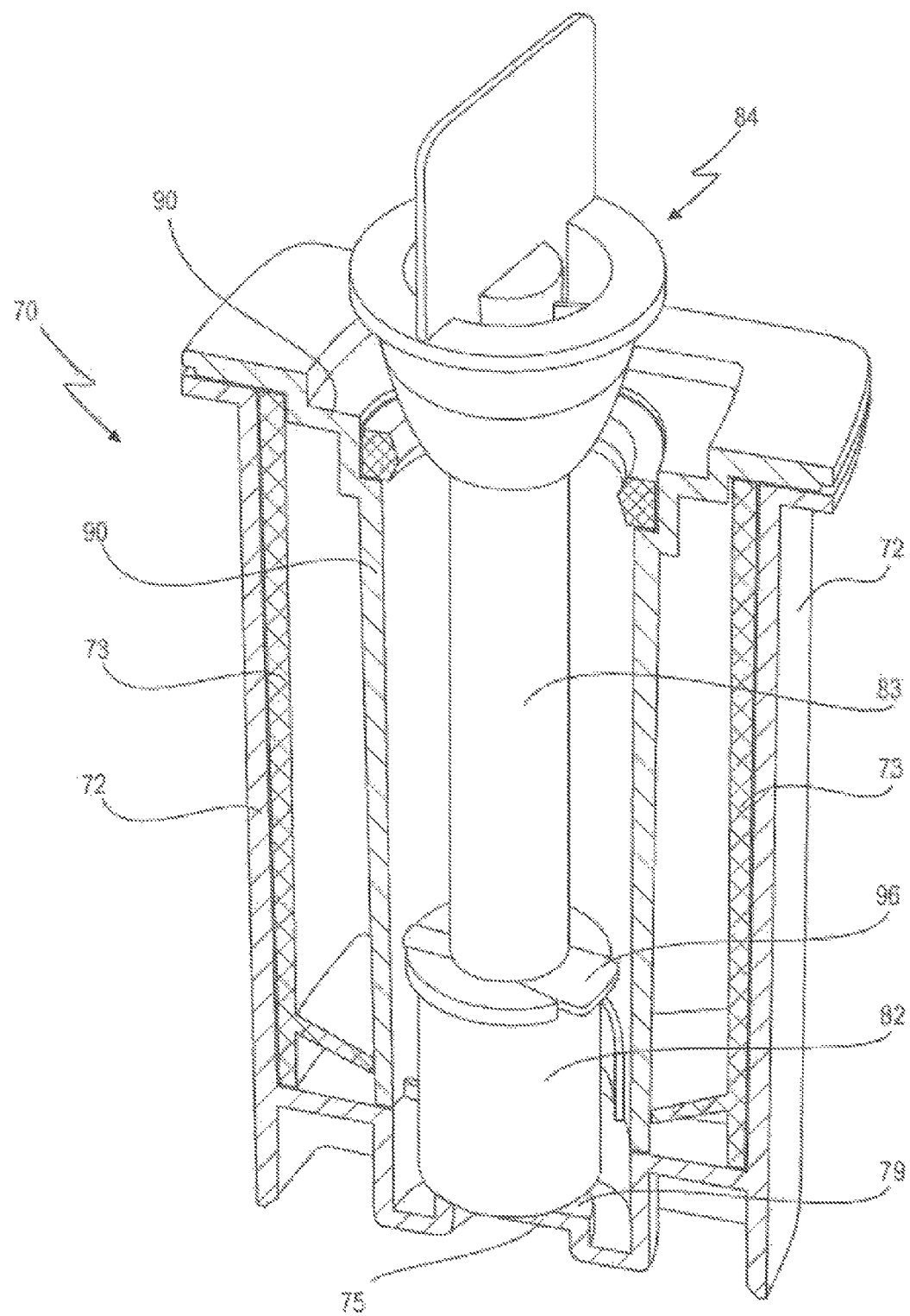
FIG. 10 shows a cross section through the assembled embodiment shown in FIG. 9.

FIG. 10 shows a cross section of the assembled device 70 from FIG. 9, i.e., the device 70 in which the sampling element 80 has been inserted, or is in the process of being inserted, together with the insertion element 90 into the container 72 in which the holding element 73 is also already arranged. In FIG. 10 it can be seen that the base 75 of the container 72 is provided with an elevation 79 onto which the sampler 82 can be compressed. In the region 96 of the sampling element 80, further means may be provided, interacting with fixing means, for example a thread inside or on the inner side of the container or the holding element, in order to bring about fixing of the sampling element. The elevation 79 represented in FIG. 10 may likewise have ridge-shaped ribs, which however are not represented in FIG. 10 for better clarity.

To assemble the device 70, first the holding element 73 is inserted into the container 72. Access to the elevation 79 on the base 75 of the container 72 is ensured by the holding element opening 76 provided in the lower end of the holding element. This can be followed by inserting the insertion element 90 which, as can be seen in FIG. 9D, has two lateral flanges or a peripheral edge which comes to lie on the upper edge of the container 78 (see FIG. 9A) and thereby limits the insertion of the insertion element 90 into the container 72. The insertion element 90, which is of a substantially cylindrical design, has at the lower end, facing the base 75 of the container 72, the open end 94, through which access to the elevation 79 on the base 75 of the container 72 is ensured for the sampler 82 that is to be squeezed out on it. Insertion of the sampling element 80 has the effect that the end section 84 seals off the opening 92 in the insertion element 90 in a sealing manner by means of the sealing ring 86 and thereby closes the device 70. At the same time, the sampler 82 is compressed on the elevation 79, so that the sample previously taken up in it, in particular saliva sample, is squeezed out on the elevation 79.

Figure 11:
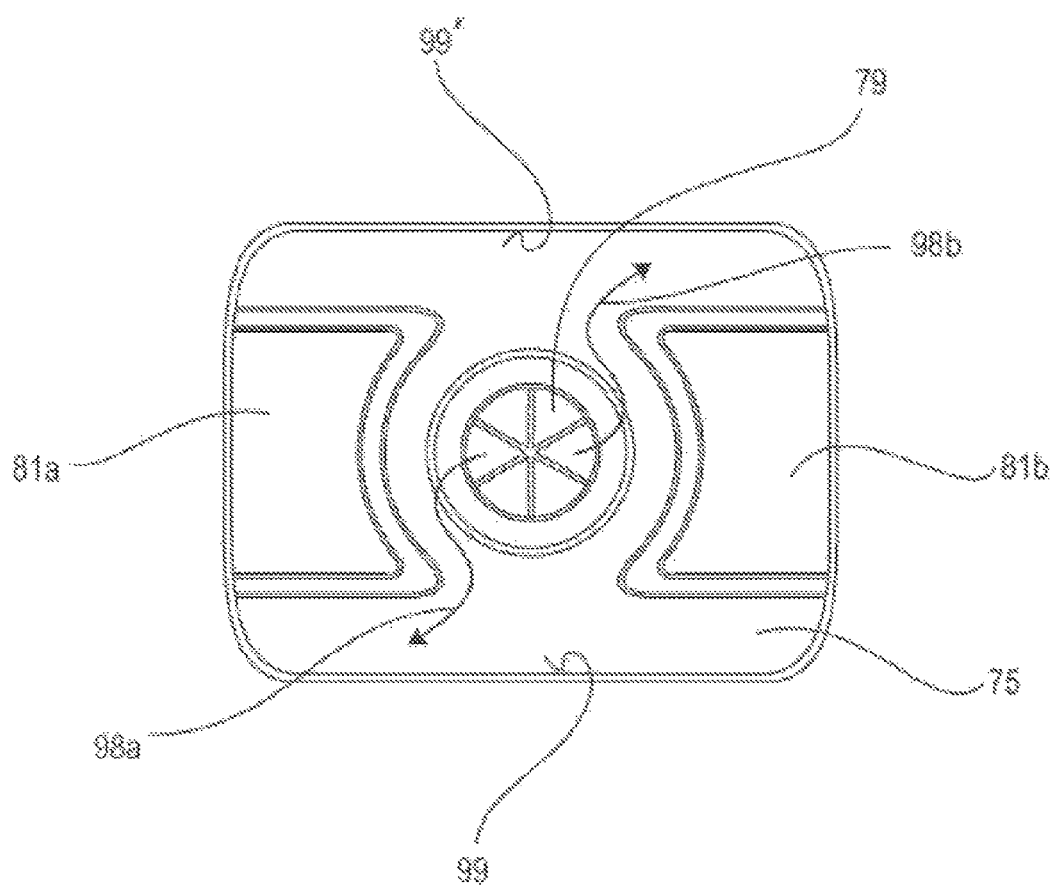
FIG. 11 shows a plan view of the base of the container of the embodiment shown in FIGS. 9 and 10.

A plan view of the base 75 of the container 72 is shown in FIG. 11, the peripheral circumferential surface 76 not being represented for reasons of clarity.

As can be seen in FIG. 11, centrally on the base 75 there is a hemispherical elevation 79, onto which the sampler 82 can be squeezed out. Also on the base there are lateral elevations 81a and 81b, which are formed at a distance from the elevation 79 and adjoining the short side walls of the substantially rectangular base 75. By the elevations 81a and 81b, the sample or saliva running off over the elevation 79 is respectively guided laterally to the long side edges of the base 75, as shown by the arrows 98a and 98b. The absorbent sections of the test strips 18 protrude into these side edges of the base 75, so that the sample can reach the test strips via these absorbent sections and the test can thereby be started.

It will be appreciated that the container is made of a transparent material, preferably plastic, in order to be able to read off the test result on the test strips 18 visually or mechanically with a scanner.

It will be appreciated that the device is not limited to the embodiments described above. In particular, the number of test strips can vary as required, and the structure of the container is also variable and does not necessarily have to be in the form of a container with a circular cross section. Accordingly, the configuration of the holding element can also differ from the one described in the embodiments. Instead of the semicircular, curved shape illustrated here, it is possible in particular for the holding element to have a tubular shape and thus bear about the full circumference of the circle on the inner face of the circumferential surface. It is also conceivable for the lid of the container to be replaced by another closure element, in particular by a closable flap. The cover element too is not limited to a three-part structure, and instead it can also be in the form of a multi-part or just one-part or two-part cover element.

Irrespective of the particular embodiment, the device according to the invention can be used for any type of test for a drug or for multiple drugs. The sample of fluid can be tested at one and the same time for several drugs, including amphetamines (AMP 1000), barbiturates (BAR 300), benzodiazepines (BZD 300), cocaine (COC 300), marihuana (THC 50), methadone (MTD 300), methamphetamine (MET 1000), methylenedioxy-methamphetamine (MDMA 500), morphine (MOR 300), opiates (OPI 2000), oxycodone (OXY 100), phencyclidine (PCP 25), propoxyphene (PPX 300), tricyclic antidepressants (TCA 1000), buprenorphine (BUP 10), cotinine (COT 200), EDDP (EDDP 100) and fentanyl (FYL 10). An alcohol test and at least one adulteration test can be integrated into the device.

The main advantages of the invention are the simple handling of the device according to the invention and the possibility of being able to send the sample to a certified laboratory without exchanging any elements and without removing the test strips. This permits quick, hygienic and more reliable implementation of the test and does not require any special knowledge on the part of the person conducting the test.

What is claimed is:
1. A device for determining the presence of one or more analytes in a sample of human body fluid, comprising:
a container for receiving a sample of body fluid, an interior that is delimited by a base and by a circumferential surface, the circumferential surface having an inner face;

a plurality of test strips, each including an absorbent section and reagents for determining a presence of analytes in the sample of body fluid;

a holding element for receiving and holding the plurality of test strips at the inner face, said holding element having a shape corresponding to the inner face of the circumferential surface of the container; and an elongate sampling element including an insertion element and an absorbent sampler at a first end of the insertion element, the absorbent sampler being insertable into the container for transfer of the sample of body fluid into the container wherein the body fluid may be absorbed by the plurality of test strips, wherein at least one of the insertion elements and the absorbent sampler includes an indicator for indication of the presence of the liquid sample of sufficient quantity for the carrying out of the assay for determining the presence of the analytes in the sample.

2. The device of claim 1, wherein the plurality of test strips are configured to determine respective amounts of the analytes.

3. The device of claim 1, wherein the indicator comprises a strip of an absorbent material present in the sampling element.

4. The device of claim 3, wherein the indicator strip is included as a zone on the test strip.

5. The device according to claim 1, wherein the sampling element has a marking for indicating the minimum travelling distance of the sample of body fluid through the indicator strip.

6. The device of claim 1, wherein the holding element is shaped with pretensioning and clamped into the container.

7. The device of claim 1, wherein the holding element is at least partially bonded to the circumferential surface on the inside of at least one of the container and the base.

8. The device of claim 1, wherein the insertion element includes a second end opposite the first end, the second end being operatively coupled with a closure for closing the container and blocking the removal of the sampling element from the container after the sampling element has been introduced into the container, the closure including a pierceable self-sealing sampling element for permitting, after it has been pierced, access to the interior of the container while the closure remains fitted onto the container.

9. A device for indicating the presence of an amount of liquid sample sufficient for carrying out an assay, comprising:
a stem section defining a longitudinal axis and having a proximal end and a distal end, the stem section including a recess extending along the longitudinal axis;

a grip disposed on the proximal end of the stem section;
an absorbent sampling element disposed on the distal end of the stem section; and
a removable indicator strip of an absorbent material and having a distal end, the removable indicator strip disposed in the recess so that the distal end of the indicator strip protrudes into the absorbent sampling element,
wherein the indicator strip includes an indication zone that lies at a specific distance away from the absorbent sampling element for detection of a sufficient amount liquid sample.

10. The device of claim 9, wherein the indication zone changes color when the liquid sample enters the indication zone.

11. A device for determining the presence of one or more analytes in a sample of human body fluid, comprising:
a container for receiving a sample of body fluid;
the container having a base and opposing planar forward and rearward outer walls, the opposing forward and rearward walls positioned with a slight inward cant narrowing toward the base; and a pair of side walls joining the opposing walls and having an arcuate shape when viewed from above the container, the forward, rearward, and pair of side walls defining an upper periphery;
a panel portion positioned at the forward wall for securing a plurality of test strips between the forward wall and the panel portion, the test strips each including an absorbent section and reagents for determining a presence of one or more analytes in the sample of body fluid;
a top panel traversing the upper periphery,
a tubular portion extending downwardly between the top panel and the base, and
an elongate sampling element including an insertion element and an absorbent sampler at a first end of the insertion element, the absorbent sampler being insertable into the tubular portion and engageable with a surface extending transverse to the tubular portion extending downwardly, for transfer of the sample of body fluid from the absorbent sampler into the container for contacting lower ends of the plurality of test strips.

12. The device of claim 11 further wherein at least one of the insertion element and the absorbent sampler includes an indicator for indication of the presence of the liquid sample sufficient for determining the presence of one or more analytes in the sample.

13. The device of claim 11 wherein the surface extending transverse to the tubular portion extending downwardly is part of a pedestal portion extending upwardly from the base of the container.

* * * * *